(12) United States Patent
Mahapatra et al.

(10) Patent No.: US 9,314,265 B2
(45) Date of Patent: *Apr. 19, 2016

(54) ACCESS NEEDLE PRESSURE SENSOR DEVICE AND METHOD OF USE

(75) Inventors: Srijoy Mahapatra, Edina, MN (US); George Gillies, Charlottesvile, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/607,993

(22) Filed: Sep. 10, 2012

(65) Prior Publication Data

US 2012/0330184 A1 Dec. 27, 2012

Related U.S. Application Data

(63) Continuation of application No. 12/530,830, filed as application No. PCT/US2008/056643 on Mar. 12, 2008, now Pat. No. 8,282,565.

(60) Provisional application No. 60/918,782, filed on Mar. 19, 2007.

(51) Int. Cl.
*A61B 17/34* (2006.01)
*A61B 5/00* (2006.01)
(Continued)

(52) U.S. Cl.
CPC ............ *A61B 17/3401* (2013.01); *A61B 5/4887* (2013.01); *A61B 5/6848* (2013.01);
(Continued)

(58) Field of Classification Search
CPC .......... A61B 5/03; A61B 5/0456; A61B 5/06; A61B 5/4887; A61B 5/6848; A61B 5/6869; A61B 17/3401; A61B 17/34; A61B 5/0215; A61B 5/031; A61B 5/202; A61B 5/7239; A61B 17/3403; A61B 2017/00243; A61B 2019/464; A61B 2562/0247
USPC ............... 604/65–67, 272; 600/485, 486, 488
See application file for complete search history.

(56) References Cited

U.S. PATENT DOCUMENTS 3,794,026 A 2/1974 Jacobs
4,349,023 A 9/1982 Gross
(Continued)

FOREIGN PATENT DOCUMENTS

AU 70522/96 1/1997
CA 2236958 5/1998
(Continued)

OTHER PUBLICATIONS

U.S. Appl. No. 61/305,560, filed on Feb. 18, 2010.
(Continued)

*Primary Examiner* — Theodore Stigell
(74) *Attorney, Agent, or Firm* — Kilpatrick Townsend & Stockton LLP

(57) ABSTRACT

A tool and method of positioning and delivering medical devices and therapeutics within the pericardial space, as well as other body part or space. A needle is inserted into the chest through a sub-xiphoid puncture, and the pressure within the needle is monitored manometrically or otherwise sensed as the needle is advanced towards the pericardial space. By reading the pressure within the needle while it is advanced, the clinician is able to know that he or she is avoiding insertion of it into organs or spaces not intended to be the target location. In addition the retractable sharp edge allows the operator to access the space and cut tissue but do so safely by retracting the sharp edge.

20 Claims, 19 Drawing Sheets

(51) Int. Cl.
*A61B 5/0215* (2006.01)
*A61B 5/03* (2006.01)
*A61B 5/20* (2006.01)
*A61B 17/00* (2006.01)
*A61B 19/00* (2006.01)

(52) U.S. Cl.
CPC ............. *A61B5/6869* (2013.01); *A61B 17/34* (2013.01); *A61B 5/0215* (2013.01); *A61B 5/031* (2013.01); *A61B 5/202* (2013.01); *A61B 5/7239* (2013.01); *A61B 17/3403* (2013.01); *A61B 2017/00243* (2013.01); *A61B 2019/464* (2013.01); *A61B 2562/0247* (2013.01)

(56) References Cited

U.S. PATENT DOCUMENTS

| | | |
|---|---|---|
| 4,607,644 A | 8/1986 | Pohndorf |
| 4,817,634 A | 4/1989 | Holleman |
| 4,971,070 A | 11/1990 | Holleman |
| 4,991,603 A | 2/1991 | Cohen |
| 5,033,477 A | 7/1991 | Chin |
| 5,071,428 A | 12/1991 | Chin |
| 5,213,570 A | 5/1993 | VanDeripe |
| 5,269,326 A | 12/1993 | Verrier |
| 5,300,110 A | 4/1994 | Latterell |
| 5,335,313 A | 8/1994 | Douglas |
| 5,336,252 A | 8/1994 | Cohen |
| 5,395,349 A | 3/1995 | Quiachon |
| 5,465,711 A | 11/1995 | Moll |
| 5,484,423 A | 1/1996 | Waskonig |
| 5,509,924 A | 4/1996 | Paspa |
| 5,544,654 A | 8/1996 | Murphy |
| 5,669,882 A | 9/1997 | Pyles |
| 5,679,005 A | 10/1997 | Einstein |
| 5,702,438 A | 12/1997 | Avitall |
| 5,725,504 A | 3/1998 | Collins |
| 5,733,280 A | 3/1998 | Avitall |
| 5,779,699 A | 7/1998 | Lipson |
| 5,797,870 A | 8/1998 | March |
| 5,800,428 A | 9/1998 | Nelson |
| 5,812,978 A | 9/1998 | Nolan |
| 5,827,216 A | 10/1998 | Igo |
| 5,843,048 A | 12/1998 | Gross |
| 5,846,239 A | 12/1998 | Swanson |
| 5,885,217 A | 3/1999 | Gisselberg |
| 5,916,194 A | 6/1999 | Jacobsen |
| 5,931,810 A | 8/1999 | Grabek |
| 5,970,457 A | 10/1999 | Brant |
| 5,972,013 A | 10/1999 | Schmidt |
| 6,036,685 A | 3/2000 | Mueller |
| 6,051,008 A | 4/2000 | Saadat |
| 6,123,084 A | 9/2000 | Jandak |
| 6,148,825 A | 11/2000 | Anderson |
| 6,156,009 A | 12/2000 | Grabek |
| 6,156,018 A | 12/2000 | Hassett |
| 6,162,195 A | 12/2000 | Igo |
| 6,200,303 B1 | 3/2001 | Verrier |
| 6,206,004 B1 | 3/2001 | Schmidt |
| 6,231,518 B1 | 5/2001 | Grabek |
| 6,234,804 B1 | 5/2001 | Yong |
| 6,237,605 B1 | 5/2001 | Vaska |
| 6,263,241 B1 | 7/2001 | Rosborough |
| 6,266,567 B1 | 7/2001 | Ishikawa |
| 6,270,476 B1 | 8/2001 | Santoianni |
| 6,270,484 B1 | 8/2001 | Yoon |
| 6,273,877 B1 | 8/2001 | West |
| 6,278,975 B1 | 8/2001 | Brant |
| 6,314,963 B1 | 11/2001 | Vaska |
| 6,322,536 B1 | 11/2001 | Rosengart |
| 6,325,776 B1 | 12/2001 | Anderson |
| 6,416,505 B1 | 7/2002 | Fleischman |
| 6,423,051 B1 | 7/2002 | Kaplan |
| 6,500,130 B2 | 12/2002 | Kinsella |
| 6,527,767 B2 | 3/2003 | Wang |
| 6,551,289 B1 | 4/2003 | Higuchi |
| 6,554,809 B2 | 4/2003 | Aves |
| 6,558,382 B2 | 5/2003 | Jahns |
| 6,569,082 B1 | 5/2003 | Chin |
| 6,592,552 B1 | 7/2003 | Schmidt |
| 6,613,062 B1 | 9/2003 | Leckrone |
| 6,616,676 B2 | 9/2003 | Bashiri |
| 6,666,844 B1 | 12/2003 | Igo |
| 6,666,861 B1 | 12/2003 | Grabek |
| 6,689,128 B2 | 2/2004 | Sliwa |
| 6,711,436 B1 | 3/2004 | Duhaylongsod |
| 6,723,092 B2 | 4/2004 | Brown |
| 6,752,805 B2 | 6/2004 | Maguire |
| 6,771,996 B2 | 8/2004 | Bowe |
| 6,783,510 B1 | 8/2004 | Gibson |
| 6,786,898 B2 | 9/2004 | Guenst |
| 6,811,544 B2 | 11/2004 | Schaer |
| 6,827,714 B2 | 12/2004 | Swanson |
| 6,827,715 B2 | 12/2004 | Francischelli |
| 6,835,193 B2 | 12/2004 | Epstein |
| 6,837,848 B2 | 1/2005 | Bonner |
| 6,837,886 B2 | 1/2005 | Collins |
| 6,849,075 B2 | 2/2005 | Bertolero |
| 6,868,291 B1 | 3/2005 | Bonner |
| 6,869,414 B2 | 3/2005 | Simpson |
| 6,876,885 B2 | 4/2005 | Swoyer |
| 6,899,710 B2 | 5/2005 | Hooven |
| 6,916,318 B2 | 7/2005 | Francischelli |
| 6,918,890 B2 | 7/2005 | Schmidt |
| 6,918,908 B2 | 7/2005 | Bonner |
| 6,921,295 B2 | 7/2005 | Sommer |
| 6,928,313 B2 | 8/2005 | Peterson |
| 6,936,040 B2 | 8/2005 | Kramm |
| 6,960,205 B2 | 11/2005 | Jahns |
| 6,968,223 B2 | 11/2005 | Hanover |
| 6,973,352 B1 | 12/2005 | Tsutsui |
| 6,974,454 B2 | 12/2005 | Hooven |
| 7,004,937 B2 | 2/2006 | Lentz |
| 7,008,418 B2 | 3/2006 | Hall |
| 7,027,876 B2 | 4/2006 | Casavant |
| 7,037,296 B2 | 5/2006 | Kadziauskas |
| 7,041,099 B2 | 5/2006 | Thomas |
| 7,059,878 B1 | 6/2006 | Hendrixson |
| 7,063,693 B2 | 6/2006 | Guenst |
| 7,085,606 B2 | 8/2006 | Flach |
| 7,089,063 B2 | 8/2006 | Lesh |
| 7,090,637 B2 | 8/2006 | Danitz |
| 7,101,362 B2 | 9/2006 | Vanney |
| 7,104,986 B2 | 9/2006 | Hovda |
| 7,120,504 B2 | 10/2006 | Osypka |
| 7,130,699 B2 | 10/2006 | Huff |
| 7,142,919 B2 | 11/2006 | Hine |
| 7,146,225 B2 | 12/2006 | Guenst |
| 7,147,633 B2 | 12/2006 | Chee |
| 7,207,988 B2 | 4/2007 | Leckrone |
| 7,214,180 B2 | 5/2007 | Chin |
| 7,226,448 B2 | 6/2007 | Bertolero |
| 7,226,458 B2 | 6/2007 | Kaplan |
| 7,232,422 B2 | 6/2007 | Gibson |
| 7,247,139 B2 | 7/2007 | Yudkovitch |
| 7,259,906 B1 | 8/2007 | Islam |
| 7,264,587 B2 | 9/2007 | Chin |
| 7,286,992 B2 | 10/2007 | Sander |
| 7,309,328 B2 | 12/2007 | Kaplan |
| 7,398,781 B1 | 7/2008 | Chin |
| 7,468,029 B1 | 12/2008 | Robertson |
| 7,473,244 B2 | 1/2009 | Frazier |
| 8,282,565 B2 * | 10/2012 | Mahapatra et al. ........... 600/486 |
| 2001/0020166 A1 | 9/2001 | Daly |
| 2001/0039410 A1 | 11/2001 | Verrier |
| 2002/0045895 A1 | 4/2002 | Sliwa |
| 2002/0055714 A1 | 5/2002 | Rothschild |
| 2002/0058925 A1 | 5/2002 | Kaplan |
| 2002/0072737 A1 | 6/2002 | Belden |
| 2002/0082523 A1 | 6/2002 | Kinsella |
| 2002/0161361 A1 | 10/2002 | Sherman |
| 2003/0028187 A1 | 2/2003 | Vaska |
| 2003/0065318 A1 | 4/2003 | Pendekanti |
| 2003/0069572 A1 | 4/2003 | Wellman |

(56) References Cited

U.S. PATENT DOCUMENTS

| | | |
|---|---|---|
| 2003/0114796 A1 | 6/2003 | Schmidt |
| 2003/0181855 A1 | 9/2003 | Simpson |
| 2004/0024397 A1 | 2/2004 | Griffin |
| 2004/0024413 A1 | 2/2004 | Lentz |
| 2004/0024435 A1 | 2/2004 | Leckrone |
| 2004/0034365 A1 | 2/2004 | Lentz |
| 2004/0064138 A1 | 4/2004 | Grabek |
| 2004/0087831 A1 | 5/2004 | Michels |
| 2004/0087938 A1 | 5/2004 | Leckrone |
| 2004/0102804 A1 | 5/2004 | Chin |
| 2004/0126746 A1 | 7/2004 | Toly |
| 2004/0138526 A1 | 7/2004 | Guenst |
| 2004/0138527 A1 | 7/2004 | Bonner |
| 2004/0138531 A1 | 7/2004 | Bonner |
| 2004/0147826 A1 | 7/2004 | Peterson |
| 2004/0176679 A1 | 9/2004 | Murphy et al. |
| 2004/0186507 A1 | 9/2004 | Hall |
| 2004/0215168 A1 | 10/2004 | Verrier |
| 2004/0216748 A1 | 11/2004 | Chin |
| 2004/0267303 A1 | 12/2004 | Guenst |
| 2004/0267326 A1 | 12/2004 | Ocel |
| 2005/0004514 A1* | 1/2005 | Hochman ................. 604/67 |
| 2005/0020914 A1 | 1/2005 | Amundson |
| 2005/0027243 A1 | 2/2005 | Gibson |
| 2005/0085769 A1 | 4/2005 | MacMahon |
| 2005/0154376 A1 | 7/2005 | Riviere |
| 2005/0215945 A1 | 9/2005 | Harris et al. |
| 2005/0234507 A1 | 10/2005 | Geske |
| 2005/0251094 A1 | 11/2005 | Peterson |
| 2005/0256368 A1 | 11/2005 | Klenk |
| 2005/0261673 A1 | 11/2005 | Bonner |
| 2005/0273006 A1 | 12/2005 | Stewart |
| 2005/0273144 A1 | 12/2005 | Lennox |
| 2006/0025705 A1 | 2/2006 | Whittaker |
| 2006/0025762 A1 | 2/2006 | Mohan |
| 2006/0041243 A1 | 2/2006 | Nayak |
| 2006/0052660 A1 | 3/2006 | Chin |
| 2006/0064056 A1 | 3/2006 | Coyle |
| 2006/0064058 A1 | 3/2006 | Coyle |
| 2006/0074397 A1 | 4/2006 | Shimada |
| 2006/0106442 A1 | 5/2006 | Richardson |
| 2006/0122591 A1 | 6/2006 | Keidar |
| 2006/0189840 A1 | 8/2006 | Walsh |
| 2006/0200002 A1 | 9/2006 | Guenst |
| 2006/0229490 A1 | 10/2006 | Chin |
| 2006/0247522 A1 | 11/2006 | McGee |
| 2006/0247672 A1 | 11/2006 | Vidlund |
| 2006/0259017 A1 | 11/2006 | Heil |
| 2006/0270900 A1 | 11/2006 | Chin |
| 2006/0271032 A1 | 11/2006 | Chin |
| 2007/0016068 A1 | 1/2007 | Grunwald |
| 2007/0016069 A1 | 1/2007 | Grunwald |
| 2007/0016070 A1 | 1/2007 | Grunwald |
| 2007/0016072 A1 | 1/2007 | Grunwald |
| 2007/0032796 A1 | 2/2007 | Chin-Chen |
| 2007/0038052 A1 | 2/2007 | Swoyer |
| 2007/0043397 A1 | 2/2007 | Ocel |
| 2007/0055142 A1 | 3/2007 | Webler |
| 2007/0198041 A1 | 8/2007 | Rupp |
| 2007/0270882 A1 | 11/2007 | Hjelle |
| 2008/0015625 A1 | 1/2008 | Ventura |
| 2008/0051671 A1 | 2/2008 | Broome |
| 2008/0091109 A1 | 4/2008 | Abraham |
| 2008/0097399 A1 | 4/2008 | Sachar |
| 2008/0108945 A1 | 5/2008 | Kaplan |
| 2008/0183080 A1 | 7/2008 | Abraham |
| 2008/0208184 A1 | 8/2008 | Davies |
| 2008/0262432 A1 | 10/2008 | Miller |
| 2008/0294174 A1 | 11/2008 | Bardsley |
| 2009/0068627 A1 | 3/2009 | Toly |
| 2009/0069697 A1 | 3/2009 | Frazier |
| 2009/0246747 A1 | 10/2009 | Buckman, Jr. |
| 2009/0253102 A1 | 10/2009 | Porikli et al. |
| 2009/0311656 A1 | 12/2009 | Lundback et al. |
| 2010/0094143 A1 | 4/2010 | Mahapatra |
| 2010/0114093 A1 | 5/2010 | Mahapatra |
| 2010/0211064 A1 | 8/2010 | Mahapatra |
| 2010/0241185 A1 | 9/2010 | Mahapatra |
| 2012/0249890 A1 | 10/2012 | Chardon et al. |
| 2012/0274863 A1 | 11/2012 | Chardon et al. |
| 2012/0278348 A1 | 11/2012 | Chardon et al. |
| 2012/0283582 A1 | 11/2012 | Mahapatra et al. |
| 2012/0310052 A1 | 12/2012 | Mahapatra |
| 2013/0108999 A1 | 5/2013 | Gillies |

FOREIGN PATENT DOCUMENTS

| | | |
|---|---|---|
| DE | 43 13 903 C1 | 9/1994 |
| EP | 0 450 608 A1 | 10/1991 |
| EP | 1 129681 | 9/2001 |
| EP | 1 181 896 | 2/2002 |
| WO | WO 87/04081 | 7/1987 |
| WO | WO 93/20878 | 10/1993 |
| WO | WO 93/20886 | 10/1993 |
| WO | WO 95/10319 | 4/1995 |
| WO | WO 95/15115 | 6/1995 |
| WO | WO 97/33526 | 9/1997 |
| WO | WO 99/18869 | 4/1999 |
| WO | WO 01/05306 | 1/2001 |
| WO | WO 01/58373 | 8/2001 |
| WO | WO 01/68173 | 9/2001 |
| WO | WO 01/80724 | 11/2001 |
| WO | WO 01/80757 | 11/2001 |
| WO | WO 01/93930 | 12/2001 |
| WO | WO 2008/112870 | 9/2008 |
| WO | WO 2008/115745 | 9/2008 |
| WO | WO 2008/118737 | 10/2008 |
| WO | WO 2009/062061 | 5/2009 |
| WO | WO 2011/103456 | 8/2011 |

OTHER PUBLICATIONS

U.S. Appl. No. 61/442,836, filed on Feb. 15, 2011.
Stokes, U.S. Statutory Invention Registration H356, Nov. 3, 1987.
DP25B-S Strain Gage Pagel Meter: User's Guide, OMEGA Engineering, Inc., 2002 (accessed Jul. 9, 2007), Stamford, CT. Online at http://www.omega.com/Manuals/manualpdf/M3598.pdf.
DP41B Universal Input Meter: User's Guide, OMEGA Engineering, Inc., 2005 (accessed Dec. 5, 2007), Stamford, CT. Online at http://www.omega.com/Manuals/manualpdf.M2544.pdf.
DPI 603 Portable Pressure Calibrator User Guide, OMEGA Engineering, Inc., 1996 (accessed Dec. 5, 2007), Stamford, CT. Online at http://www.omega.com/Manuals/manual.pdf/M2913.pdf.
PX26 Series Pressure Transducers: Instruction Sheet, Omega Engineering, Inc., 2004 (accessed Jul. 9, 2007), Stamford, CT. Online at http//www.omega.com/Pressure/pdf/PX26.pdf.
PX26 Series Pressure Transducers: Instruction Sheet, OMEGA Engineering, Inc., 2004 (accessed Dec. 5, 2007), Stamford, CT. Online at http://www.omega.com/Manuals/manualpdf/M1608.pdf.
Arrow International Corporation, AN-05505 Epidural Needle, www.arrowintl.com/products/boms/AN05505.asp?cat=17&item=AN-05505&xsec={accessed Feb. 13, 2007).
Beukema, "Radiofrequency Ablation of Atrial Fibrillation in Patients Undergoing Concomitant Cardiac Surgery. First Experience," PACE, 1997, p. 1100, vol. 20 (Part II).
D'Avila, "Transthoracic Epicardial Catheter Ablation of Ventricular Tachycardia," Heart Rhythmn, 2006, p. 1110-1111, vol. 3.
DeRose, Jr., "Robotically Assisted Left Ventricular Epicardial Lead Implantation for Biventricular Pacing: the Posterior Approach," The Annals of Thoracic Surgery, 2004, p. 1472-1474, vol. 77.
Frölich, "Pioneers in Epidural Needle Design," Anesthesia & Analgesia, 2001, p. 215-220, vol. 93.
Hansky, "Lead Selection and Implantation Technique for Biventricular Pacing," European Heart Journal Supplements, 2004, p. D112-D116, vol. 6, Supplement D.
Klein, "Radiofrequency Ablation of Cardiac Arrhythmias," Scientific American Science & Medicine, 1994, p. 48-57.
Lin, "Catheter Microwave Ablation Therapy for Cardiac Arrhythmias," Bioelectromagnetics, 1999, p. 120-132, vol. 20.

(56) References Cited

OTHER PUBLICATIONS

Mahapatra, "Access Device and Manometric Monitoring System for Epicardial Electrophysiology: Improved Porotype and use in Human Trials", Jul. 2007, Technical Report No. UVA/640419/MAE08/101.

Mahapatra, "Access Device and Manometric Monitoring System for Epicardial Electrophysiology: Improved Porotype and use in Human Trials", Jan. 2008, Technical Report No. UVA/640419/MAE08/102.

Mahapatra, "Incidence and Predictors of Cardiac Perforation after Permanent Pacemaker Placement," Heart Rhythm, 2005, p. 907-911, vol. 2, No. 9.

Mair, "Epicardial Lead Implantation Techniques for Biventricular Pacing via Left Lateral Mini-Thoracotomy, Video-Assisted Thoracoscopy, and Robotic Approach," The Heart Surgery Forum #2003-4883, 2003, p. 412-417, vol. 6 (5).

Moses, "Sirolimus-Eluting Stents Versus Standard Stents in Patients with Stenosis in a Native Coronary Artery", New England Journal of Medicine, 2003, p. 1315-1323, vol. 349, No. 14.

Packer, "Multimodality 3-D Ultrasound and Computed Tomographic Image Fusion: A Novel Basis for Catheter Navigation and Electroanatomic Mapping," 2005, Circulation, Clinical Science, Supplement 11, vol. 112, No. 17, #2939.

Sarabanda, "Efficacy and Safety of Circumferential Pulmonary Vein Isolation Using a Novel Cryothermal Balloon Ablation System" Journal of the American College of Cardiology, 2005, p. 1902-1912, vol. 46, No. 10.

Sosa, "Epicardial Mapping and Ablation Techniques to Control Ventricular Tachycardia," Journal of Cardiovascular Electrophysiology, 2005, p. 449-452, vol. 16, No. 4.

Sosa, "Nonsurgical Transthoracic Epicardial Approach in Patients with Ventricular Tachycardia and Previous Cardiac Surgery," Journal of Interventional Cardiac Electrophysiology, 2004, p. 281-288, vol. 10.

Sosa, "Percutaneous Pericardial Access for Mapping and Ablation of Epicardial Ventricular Tachycardias," Circulation, Journal of the American Heart Association, 2007, p. e542-e544, vol. 115.

Thomas, "Analysis of Human Epidural Pressures," Regional Anesthesia, 1992, p. 212-215, vol. 17, No. 4.

Tomaske, "Do Daily Threshold Trend Fluctuations of Epicardial Leads Correlate with Pacing and Sensing Characteristics in Paediatric Patients," Europace, 2007, p. 662-668, vol. 9.

U.S. Appl. No. 13/464,752, filed May 4, 2012.
U.S. Appl. No. 13/464,762, filed May 4, 2012.
U.S. Appl. No. 13/579,882, filed Nov. 29, 2012.

J. Tucker-Schwartz et al., "Improved Pressure-Frequency Sensing Subxiphoid Pericardial Access System: Performance Characteristics During In Vivo testing," IEEE Transactions on Biomedical Engineering, vol. 58, pp. 845-852 (Apr. 2011).

J. Tucker-Schwartz et al., "Pressure-Frequency Sensing Subxiphoid Access System for use in Percutaneous Cardiac Electrophysiology: Prototype Design and Pilot Study Results," IEEE Transactions on Biomedical Engineering, vol. 56, pp. 1160-1168 (May 2009).

F. Sacher, P. Maury, I. Nault, M. Wright, N. Lellouche, N. Derval, S. Ploux, M. Hocini, P. Bordachar, A. Deplagne, P. Ritter, J. Clementy, M. Haissaguerre, and P. Jais, "Prevalence of epicardial scar in patients referred for ventricular tachycardia ablation," *Heart Rhythm*, vol. 6, pp. S175-6, 2009.

C. Grimard, J. Lacotte, F. Hidden-Lucet, G. Duthoit, Y. Gallais, and R. Frank, "Percutaneous epicardial radiofrequency ablation of ventricular arrhythmias after failure of endocardial approach: a 9-year experience," *J. Cardiovasc. Electrophysiol.*, vol. 21, No. 1, pp. 56-61, 2010.

E. Aliot, W. Stevenson, J. Almendral-Garrote, F. Bogun, C. Calkins, E. Delacretaz, P. Bella, G. Hindricks, P. Jais, M. Josephson, J. Kautzner, G. Kay, K. Kuck, B. Lerman, F. Marchlinski, V. Reddy, M. Schalij, R. Schilling, L. Soejima, and D. Wilber, "EHRA/HRS expert consensus on catheter albation of ventricular arrhythmias," *Europace*, vol. 11, No. 6, pp. 771-817, 2009.

E. Sosa, M. Scanavacca, A. d'Avila, and F. Pilleggi, "A new technique to perform epicardial mapping in the electrophysiology laboratory," *J. Cardiovasc. Electrophysiol.*, vol. 7, No. 6, pp. 531-6, 1996.

E. Sosa, M. Scanavacca, A. d'Avila, J. Piccioni, O. Sanchez, J. Velarde, M. Silva, and B. Reolao, "Endocardial and epicardial ablation guided by nonsurgical transthoracic epicardial mapping to treat recurrent ventricular tachycardia," *J. Cardiovasc. Electrophysiol.*, vol. 9, No. 3, pp. 229-39, 1998.

E. Sosa, M. Scanavacca, A. d'Avila, F. Oliviera, and J. Ramires, "Nonsurgical transthoracic epicardial catheter ablation to treat recurrent ventricular tachycardia occuring late after myocardial infarction," *J Am. Coll. Cardiol.*, vol. 35, No. 6, pp. 1442-9, 2000.

U. Tedrow and W. Stevenson, "Strategies for epicardial mapping and ablation of ventricular tachycardia," *J. Cardiovasc. Electrophysiol.*, vol. 20, No. 6, pp. 710-3, 2009.

S. Mahapatra, J. Tucker—Schwartz, D. Wiggins, G. Gillies, P. Mason, G. McDaniel, D. Lapar, C. Stemland, E. Sosa, J. Ferguson, T. Bunch, G. Ailawadi, and M. Scanavacca, "Pressure frequency characteristics of the pericardial space and thorax during subxiphoid access for epicardial ventricular tachycardia ablation," *Heart Rhythm*, vol. 7, No. 5, pp. 604-9, 2010.

Office Action in U.S. Appl. No. 13/464,762 mailed Mar. 6, 2014.
Office Action in U.S. Appl. No. 13/464,752 mailed May 4, 2014.
Office Action in U.S. Appl. No. 13/464,752 mailed Dec. 4, 2014.

* cited by examiner

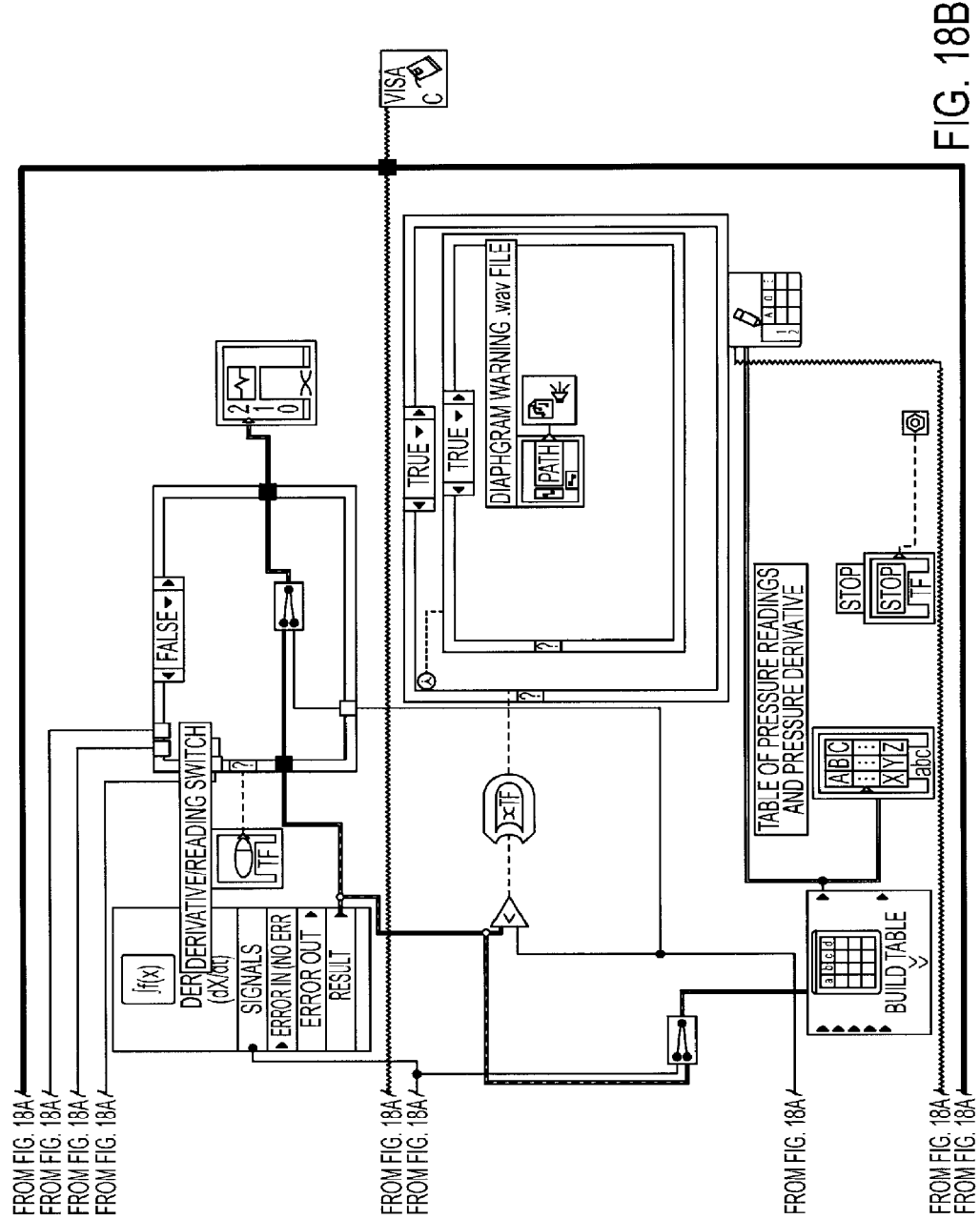

ACCESS NEEDLE PRESSURE SENSOR DEVICE AND METHOD OF USE

RELATED APPLICATIONS

The present application is a continuation of U.S. Pat. No. 8,282,565, issued Oct. 9, 2012 entitled "Access Needle Pressure Sensor Device and Method of Use," which is a national stage filing of International Application No. PCT/US2008/056643, filed Mar. 12, 2008, which claims priority under 35 U.S.C. §119(e) from U.S. Provisional Application Serial No. 60/918,782, filed Mar. 19, 2007, entitled "Manometrically Monitored Introducer Needle and Method of Use," the disclosures of which are hereby incorporated by reference herein in their entirety.

BACKGROUND OF THE INVENTION

The pericardium or epdicardium are seen as the next frontier in heart therapy. It is possible to deliver drugs to the area and affect the heart without affecting other organs. Multiple groups have also ablated arrythmias from this region. However, a major barrier is that there is not a single tool designed specifically to access the epicardium. In fact currently the epicardium is typically accessed using a lumbar puncture needle which currently carries a high complication rate, thus limiting its use to expert centers only.

However, existing medical devices that can be used to obtain pericardial access, such as epidural needles and the like, are not designed to provide the clinician with an appropriate assessment of the pressures local to the needle tip during the process of advancing them into the pericardial space. For instance, those skilled in the art may recognize that the devices and methods taught in U.S. Pat. Nos. 7,101,362; 7,037,296; 6,554,809; 6,551,289; 6,273,877; 5,843,048; 5,725,504; 5,669,882; 5,484,423 and 4,349,023, all of which are incorporated by reference herein in their entirety, reflect standard usage of an elongated fluid sampling or delivery needle having a distal end and a proximal end, but which said devices are not optimized for use as pressure-sensing guideways for a sheath/catheter means within the pericardium. Commercially available needles, such as the Arrow International Corporation model AN-05505 Epidural Needle now in clinical use, are representative in design and function of this class of devices and reflect the limitations cited above with regard to pericardial access.

To overcome the limitations of using lumbar puncture needles and to take advantage of the above physiologic properties, various aspects of the embodiments of the present invention device and method of use have been provided.

BRIEF SUMMARY OF INVENTION

The applicants have discovered that the various organs and spaces within the chest cavity are subject to different levels of superimposed hydrostatic pressure during cycles of respiration, heartbeat and peristalsis. For instance, the wall of the stomach (and hence the diaphragm) bounds an internal region of generally positive pressure, while the lung is normally at 5 to 10 atmospheres of negative pressure, and typically there is 14 mm Hg of pressure inside of the heart. Further, the pressure just outside the heart (the epicardial space) is typically close to the lung pressure. In patients that are intubated (which is typical for conventional procedures) the pressure in the lung is positive 5-12 mmHg and the inside of the heart remains at 14 mmHg. The pericardial pressure on average is the same as the lung pressure. On the other hand, the nature of the pressure within the pericardial space has heretofore been only partly understood, at best. Until now, major textbooks stated that the pressure in the lung field and the pericardial space are identical. However, the inventors recently discovered that while the mean pressures are close to the same (within 2 mmHg) the pressure frequencies are significantly different. The lung pressure frequency is 1 Hz, the pericardial pressure frequency 0.2 Hz. These physiological characteristics of the thorax provide a potentially useful set of references against which the location of the tip of a pericardial access needle can be gauged.

An aspect of an embodiment of the present invention may comprise, but not limited thereto, a needle, nominally 14 gauge in size (although other gauges, both larger and smaller, may be used instead). In some embodiments, said needle will range in length between 10 cm and 25 cm, and have markings at 1 cm intervals along its length to indicate depth of insertion. The distal tip of the needle is curved and the port hole on the end of it conforms to one of several basic designs used in the construction of this class of medical needles. The proximal end of the needle has a plurality of connectors that serve as infusion ports, a manometry port, ports or hub, a wire passage port, and other such functions. The needle is used by the interventional electrophysiologist/cardiologist or other applicable clinician as a means for accessing the pericardial space in a patient, for the purpose of placing a sheath means or catheter means within it. During the access and placement process, manometric or pressure readings are taken to insure that the distal tip of the needle is not infringing upon internal organs, structures or spaces into which it should not be pushed. Following final placement and positioning of the needle's distal tip within the pericardial space, the needle is withdrawn and a sheath means and/or catheter means are then passed over a guidewire means that had been positioned through and left in place of the needle, and said sheath means and/or catheter means are then left in place and used as needed.

A modification of the above will have a sharp needle, for example a puncture needle, hidden inside the main needle, like a stylet, obdurator or trochar. In an embodiment, for example, it could be extended no more than about 1 mm to about 3 mm to pierce, puncture or otherwise cut in or through tough tissue but would not go so far to cause damage. Therefore, the invention may be practiced with or without a puncture needle.

An aspect of various embodiments of the present invention provides a tool and method for, but not limited thereto, positioning and delivering medical devices and drugs and other therapeutics or desired/required medium within the pericardial space. A needle is inserted into the chest through a subxiphoid puncture, and the pressure within the needle is monitored manometrically or otherwise sensed as the needle is advanced towards the pericardial space. By reading the pressure within the needle while it is advanced, the clinician is able to know that he or she is avoiding insertion of it into organs or spaces not intended to be the target location, for example. In addition the retractable sharp edge of the puncture needle or the like allows the operator to access the space and cut tissue but do so safely by retracting the sharp edge.

It should be appreciated that the medium to flow through access needle or any device or system guided by the access needle may be at least one of the following: agent, substance, material, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent, or any combination thereof.

An aspect of an embodiment of the present invention provides a system for an access needle sensor device that serves as a guideway for introducing other devices into the pericardium, for instance sheath catheters that might subsequently be employed for procedures in the periardium and the epicardium of the heart. Other devices that the present invention device may accommodate include, but not limited thereto, the following: ablation catheters, guidewires, pacing leads, pacing catheters, pacemakers, visualization and recording devices, drugs, lumens, steering devices or systems, drug or cell delivery catheters, fiber endoscopes, suctioning devices, irrigation devices, electrode catheters, needles, optical fiber sensors, sources of illumination, vital signs sensors, and the like Theses devices may be deployed for procedures in an integral body part or space.

An aspect of an embodiment of the present invention provides device for accessing the thorax and middle mediastinum of a subject. The device comprising: a needle having a distal end and a proximal end; and a pressure sensor in communication with said needle for sensing pressure in the thorax or an integral body part or space.

An aspect of an embodiment of the present invention provides a method for accessing the thorax and middle mediastinum of a patient. The method comprising: inserting a needle through the thorax and the middle mediastinum; and sensing pressure in the thorax or an integral body part or space.

An aspect of the invention will be useful for heart therapy, particularly for heart rhythm therapy with ablation and pacemakers.

An aspect of the invention will be useful for accommodating the devices for delivery (or withdrawal) of drugs and other therapeutic agents to the area and affect the heart (or other body parts, space or organs) without affecting other organs.

An aspect of the invention will be useful for accommodating the devices for accommodating the practice ablating arrythmias and pacing the heart from this region. Moreover, ablation from this area may increase success rates of therapy for atrial fibrillation, ventricular tachycardia, heart failure and reduce the risk of stroke during these procedures.

An advantage associated with the present invention device and method is that it may reduce the complication rate, thus broadening beyond expert centers only, for example.

An aspect of an embodiment of the present invention provides a device for accessing one or more locations of a subject. The device comprising: a needle having a distal end and a proximal end; and a pressure sensor in communication with said needle for sensing pressure in said one or more locations.

An aspect of an embodiment of the present invention provides a method for accessing one or more locations of a patient, said method comprising: inserting a needle through the thorax and the middle mediastinum; and sensing pressure in said one or more locations.

An aspect of an embodiment of the present invention provides a device for sensing the pressure in one or more locations of a subject. The device comprising: an elongated member and having a distal end and a proximal end; and a pressure sensor in communication with the elongated member for sensing pressure in the one or more locations.

An aspect of an embodiment of the present invention provides a method for accessing one or more locations of a patient. The method comprising: inserting a needle through the thorax and the middle mediastinum; and sensing pressure in the one or more locations.

It should be appreciated that the pressure related readings and data may be received by the user, clinician, physician, or technician or the like by visual graphics, audible signals (such as voice or tones, for example) or any combination thereof. Additionally, the pressure related readings and data may be reduced to hard copy (e.g., paper) or computer storage medium. It should be appreciated that the pressure related readings and data may be transmitted not only locally, but remotely as well.

Those skilled in the art will recognize that advantages accrue from the use of the means and method of the invention, because it provides, among other things, novel and previously untaught techniques for the insertion of an access needle into the pericardium, as well other body part or space.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIGS. 18A-B are a schematic illustration of the software program assembly in its native block diagram form in a left side and right side interconnecting portions, respectively, for illustration purposes.

DETAILED DESCRIPTION OF THE EXEMPLARY EMBODIMENTS

Figure 1:
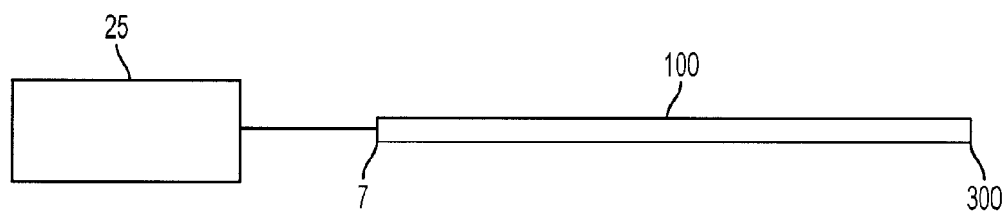
FIG. 1 is a schematic view of an embodiment of the present invention.

FIG. 1 shows an aspect of and embodiment of the invention, which comprises an access needle 100 in communication with a pressure sensor 25. The access needle has a distal end 300 and a proximal end 7. The access needle can be any needle or axial device, for example, an elongated member or the like. The needle may have at least one aperture located at the distal end of the needle; and at least one aperture located at the proximal end of the needle. It may have at least one lumen in communication with the at least one distal aperture and the at least one proximal aperture.

Figure 2:
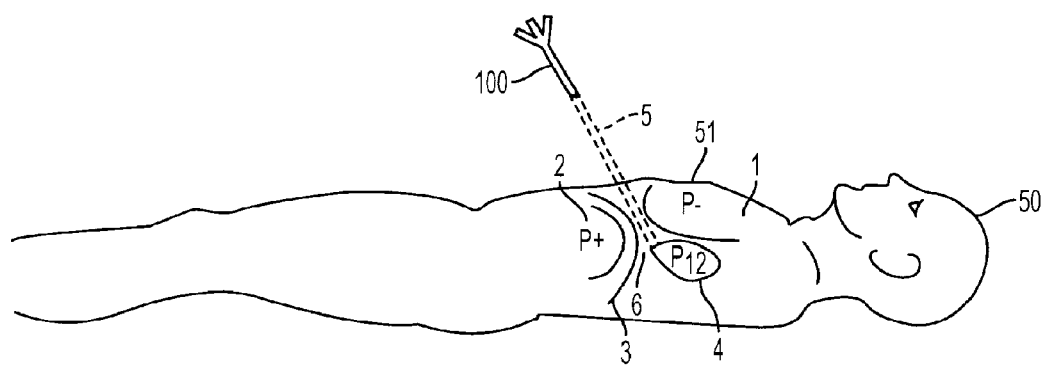
FIG. 2 is a schematic perspective view of the distribution of pressures within organs, structures and regions inside of the thorax.

FIG. 2 shows a human subject 50 undergoing insertion of an access needle 100 into the pericardial region 6 along a desired pathway 5. The access needle 100 can also be used to access the thorax 51 or the middle mediastinum of the patient 50. The access can be accomplished by an interventional procedure, such as a sub-xiphoid puncture, or a surgical procedure. It is important during the procedure that critical organs and anatomical structures within that region are not damaged by inadvertent insertion of the access needle 100 into them during the needle placement process. The physiological functions of the internal organs, spaces and structures of the body within that region occur at different levels of hydrostatic pressure. For instance, the stomach 2 exerts a positive pressure ($P_+$) on its bounding structures, including the diaphragm 3. Meanwhile, the lung 1 will function at negative pressures ($P_-$) in the range of 5 to 10 atmospheres, with the heart 4 maintaining surface pressures of approximately 12 mm Hg. Therefore, there are a variety of pressures that might be sensed by the access needle 100 during placement of it, providing that said needle 100 has a manometric functionality that could detect said pressures without damaging said organs and anatomical structures.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

In an aspect of an embodiment of the invention, the access needle 100 is used for accessing the thorax 51 and middle mediastinum of a subject 50, wherein the access needle comprises a pressure sensor or system for sensing pressure in the thorax or an integral body part or space of the thorax. However, it should be appreciated that various embodiments of the present invention device or system and method are not necessarily limited to accessing the thorax and middle mediastinum of a subject. It may also be used in the organ structures or tubular structures in the thorax as well as other locations or regions in the body. An organ includes, for example, a solid organ, a hollow organ, parenchymal tissue (e.g., stomach, brain, esophagus, colon, rectum, kidneys, liver, etc.) and/or stromal tissue. Hollow organ structures includes, for example, stomach, esophagus, colon, rectum, and ducts, or the like. A tubular structure may include a blood vessel. A blood vessel may include one or more of the following: vein, venule, artery, arterial, or capillary.

For example, in an aspect of an embodiment of the invention, the access needle 100 might be used, for instance, to measure intracranial pressure, pressure within the bladder, or even intravascular blood pressure.

Figure 3:
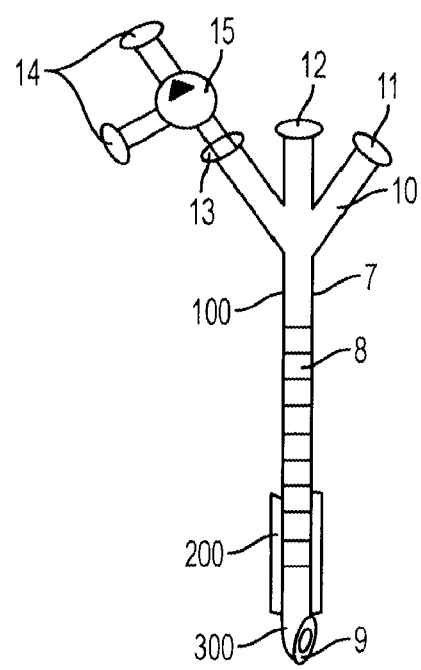
FIG. 3 is a schematic perspective view (not to scale) of the needle and its connection ports at the proximal end.

FIG. 3 shows a schematic diagram of the details of construction of one embodiment of said access needle 100. The needle 100 has a distal end 300 and a proximal end 7. In some embodiments, the needle 100 will have a length of about 10 to 25 cm and will be of about 14 gauge size, but it could be smaller or larger as suits the anatomy of the patient and the needs of the clinician using it. The needle may have markings 8 nominally at about 1 cm locations along its axial length. The markings can be used to observe the depth of insertion of the needle 100 along the pathway 5 shown in FIG. 2 or FIG. 5. At the proximal end 7 of the needle, there can be at least one aperture, such as a plurality of channels 10 that provide means for achieving the functionalities of the subject invention. These can include a port 11 to which the manometry or pressure sensing apparatus is connected and/or a port 12 into which a guidewire, sheath, catheter, puncture needle, or other devices or tools that may be inserted for passage through and withdrawal from a distal aperture, such as an end port hole 9. The puncture needle (not shown) can be in communication with a spring and used to puncture tissue of a patient. A port 13 can be connected to a multi-channel structure, conduit or connector, such as a three-way stopcock 15, for example, with inlet ports 14 to allow entry and control of the flows of infusion agents or desired fluid or medium. This flow can include providing a fluid, liquid, gas, or mixtures thereof, with or without therapeutic agents, drugs or the like, heating and/or cooling of the fluid, chemical reactions and/or physical interactions between the components of the fluid, and draining of the fluid. At the distal end 300 of said needle 100, there can be an aperture, such as a beveled end port hole 9. Said needle 100 might serve as the placement mechanism for a sheath or catheter means 200, only the distal portion of which is shown in FIG. 3. In another embodiment, the sheath or catheter means 200 can be placed inside the needle 100. In one embodiment, the needle could have a divider running the length of its axis, thus creating two or more zones, or lumens, within it. One could be used for pressure sensing, while the other could be used for passage of a guide wire, catheter, sheath, or puncture needle or other device or injection of a contrast agent or other medium. The sensing component of the needle could be much smaller in mean diameter than the other component, with the sensing orifice positioned just in front of the other component's orifice (or other locations, positions and sizes as desired or required). As a result, if the sensing component detected a perforation of the right ventricle, the resultant hole created by the puncture devices or the like would thus be small. Moreover, the entire distal tip of the inner needle assembly could also be re-shaped so that it is similar to a Tuohy needle or some other suitable configuration, thus further minimizing the risk of inadvertent perforations.

Figure 4:
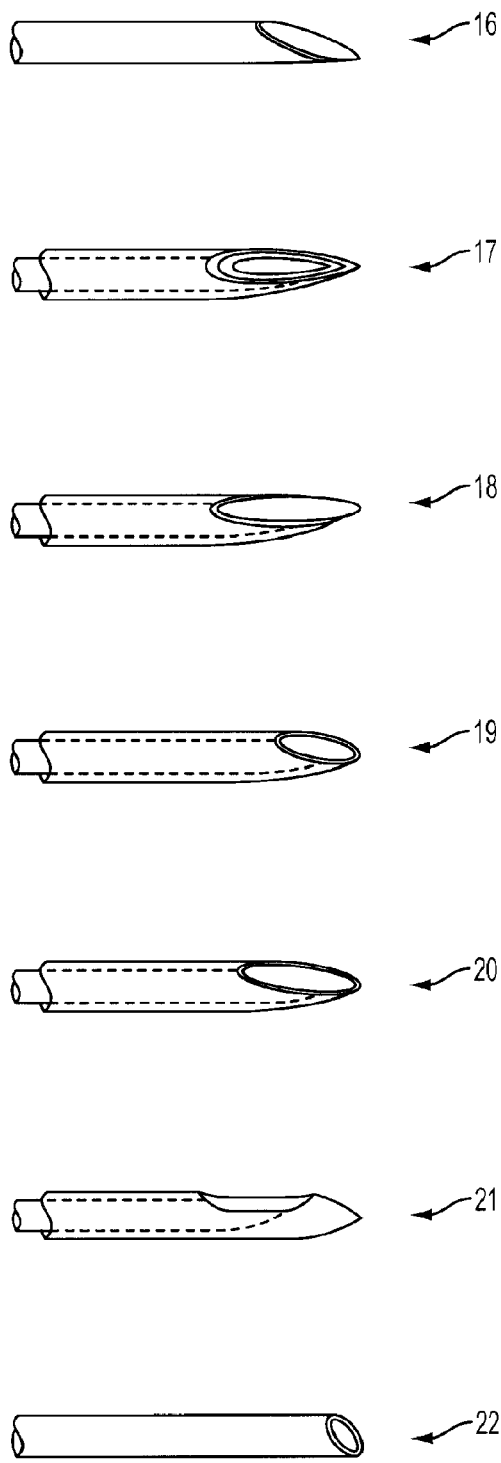
FIG. 4 is a schematic perspective view of a variety of port holes and configurations of the distal tip of the access needle.

FIG. 4 shows a series of possible configurations of the geometries and end port holes 9 of the distal ends 300 of the access needle 100. These configurations were described by Frölich and Caton in FIG. 1 of their article, "Pioneers in Epidural Needle Design, Anesthesia and Analgesia, Vol. 93, pp. 215-220, (2001), incorporated by reference herein in its entirety. The distal ends 300 are known within the field as the Barker Spinal Needle 16, the Tuohy Needle 17, the Tuohy-Flowers Needle 18, the Hustead Needle 19, the Weiss Needle 20, the Special Sprotte Needle 21, and the Crawford Needle 22. The invention may be practiced with distal ends 300 having these or other such configurations as desired or required for a given subject, region or anatomy for a medical or applicable procedure.

Figure 5:
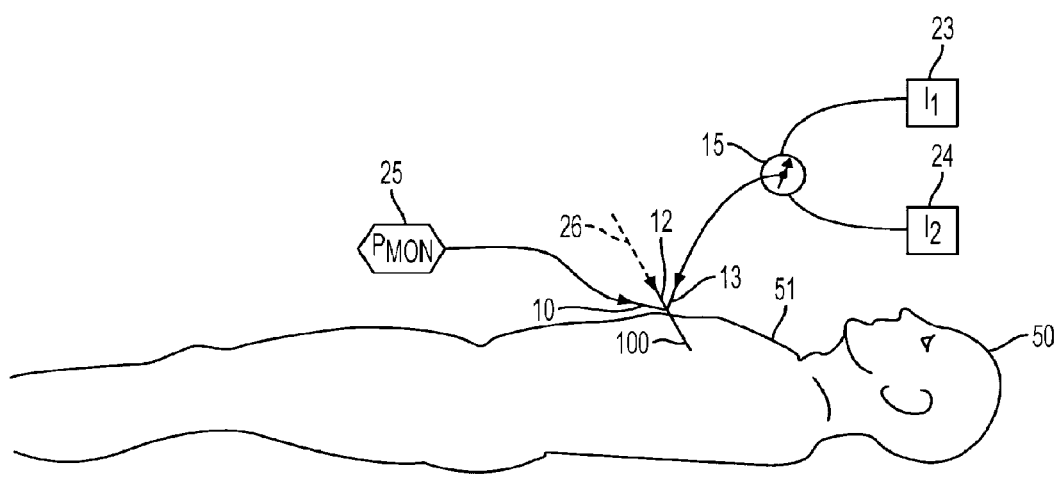
FIG. 5 is a schematic perspective view of one embodiment of the functionalities available for use with the access needle during its placement within the pericardium; or organs, structure or regions of the thorax.

FIG. 5 shows an embodiment of the access needle 100 within the thorax 51 of the patient 50. The infusion port 13 is attached to a stopcock 15 which in turn can be used to regulate or select between the flows produced by either of the infusion pumps, $I_1$ or $I_2$, 23 and 24, respectively. Another port 12 can be used to have guidewire 26 passed within it and through the distal end 300 of the needle 100. To the remaining port 10 is attached the pressure sensor, or pressure monitoring means 25 $P_{Mon}$. The pressure monitoring means 25 can be of many standard types as practiced in the art, including (but not limited to) manometric sensors of fluid pressures and levels, solid state sensors of pressure, strain gauges, optical pressure sensors, or other such means as appropriate to the practice of the invention. In an embodiment of the manometric sensor invention, the inner lumen or plurality of lumens of said needle is filled with an incompressible fluid, such as saline or water. When the distal end 300 of said needle 100 is brought into contact with an organ or anatomical structure within the thorax 51 (or other regions, organs or body parts of the subject), the pressure exerted by said incompressible fluid on said sensor means at the proximal end 7 of said needle 100 will be an indication of the nature of the organ or anatomical structure being touched. Navigation of the thorax or middle mediastinum (or other regions, organs or body parts of the subject) is enabled by pressure readings from the pressure monitoring means 25. In one embodiment, the pressure sensor does not provide a highly accurate measurement of the pressure, but instead is simply capable of differentiating positive from negative pressures. In another embodiment, the pressure sensor can be in or near the distal tip of said needle means. In still another embodiment, said incompressible fluid within said needle means might be bounded by a diaphragm or some other thin cap positioned on the distal tip of said needle means.

Generally referring to FIGS. 2, 3 and 5, and throughout this document, an embodiment of the invention comprises a device for accessing the thorax and middle mediastinum of a subject, for example (or other locations of a subject). The device may comprise a needle having a distal end and a proximal end and a pressure sensor in communication with the needle for sensing pressure in the thorax or an integral body part or space. The middle mediastinum may include the pericardial space. Another embodiment may further comprise an aperture located at the distal end of the needle and at least one aperture located at the proximal end of the needle. At least one of the proximal apertures may comprise a Luer fitting or some other suitable medical connection means. One embodiment may further comprise a multi-channel connector in communication with at least one of the proximal apertures. The multi-channel connector can comprise a stopcock or other connector means. In another embodiment, the device further comprises a guide wire that can be inserted through at least one proximal aperture and withdrawn from the distal aperture. The device can further comprise a puncture needle coaxially aligned with the needle. One embodiment further comprises a spring or other restoring force device in communication with the puncture needle. The distal aperture may comprise a configuration having at least one of the following: the Barker Needle, the Tuohy Needle, the Tuohy-Flowers Needle, The Hustead Needle, the Weiss Needle, the Special Sprotte Needle, the Crawford Needle, or other such medical devices, or any combination thereof. The pressure sensor can comprise at least one of the following: manometric, solid-state, strain gauge, optical in nature, or otherwise sensitive to hydrostatic and hydrodynamic pressures. The pressure sensor can also be able to indicate regions of positive pressure and those of negative pressure. In one embodiment, the multi-channel connector comprises a control means for regulating infusion or flow of agents or other medium to be delivered through the needle. The invention can further comprise a control means in communication with the device for regulating infusion flow to be delivered through the needle. In one embodiment, at least one marking or scale indicator is located on the needle. The device can also be adapted to be visible on a medical imaging modality, such as at least one of magnetic resonance imaging, computed tomography, fluoroscopy, or other radiological modalities. The pressure sensor can be configured to provide pressure readings for navigating the needle. In some embodiments, the needle provides a guideway for the positioning of at least one of a guide wire, a sheath or a catheter for use in medical procedures. In other embodiments, the guideway provides coaxial alignment for the at least one of guide wire, sheath or catheter, which can be inside or outside the needle. The at least one guide wire, sheath, or catheter can also be coaxially aligned with one another. One embodiment of the invention involves accessing the thorax and middle mediastinum (or other regions, organs or body parts of the thorax, as well as other parts of the subject) of a subject with an interventional procedure, such as insertion of the needle through the sub-xyphoid area of the patient. In one embodiment, the device further comprises a plurality of distal apertures. In another embodiment, multiple lumens are configured between the plurality of distal apertures and plurality of the proximal apertures. It should be appreciated that coaxial alignment does not need to be exact, but rather one conduit, lumen, sheath, or guidewire slid outside or inside of another.

An embodiment of the present invention is a method for accessing the thorax and middle mediastinum of a patient, for example (or other locations of a subject). The method may comprises of inserting a needle through the thorax and the middle mediastinum and sensing pressure in the thorax or an integral body part or space. Said sensing of pressure can be provided by a pressure sensor. The middle mediastinum may include the pericardial space. Another embodiment further comprises inserting a guide wire into said needle. Said method can also further comprise placing a sheath or catheter on said guide wire or needle. In another embodiment, said method further comprises piercing, puncturing or otherwise penetrating the tissue of the subject, which can be provided by a puncture needle. Said sensing of pressure can comprise the indication of regions of positive pressure as well as those of negative pressure. In one embodiment, said method further comprises regulating infusion flow to be delivered through said needle. In another embodiment, said method further comprises imaging said needle with at least one of magnetic resonance imaging, computed tomography, fluoroscopy, or other radiological modalities. In some embodiments, readings are provided from said sensing of pressure for navigating said needle access.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware.

Moreover, it should be appreciated that any of the components or modules referred to with regards to any of the present invention embodiments discussed herein, may be a variety of materials and/or composites as necessary or required. Still further, it should be appreciated that any of the components or modules (or combination thereof) may provide shape, size and volume contoured by adjusting its geometry and flexibility/rigidity according to the target location or anatomy (or region, including structure and morphology of any location) being treated.

EXAMPLES AND EXPERIMENTAL RESULTS

Practice of the invention will be still more fully understood from the following examples and experimental results, which are presented herein for illustration only and should not be construed as limiting the invention in any way.

Example/Experimental Result No. 1

A prototype termed "EpiNeedle" and the pressure measurement system was used in preliminary human trials (three patients) during the course of epicardial procedures.

Figure 6:
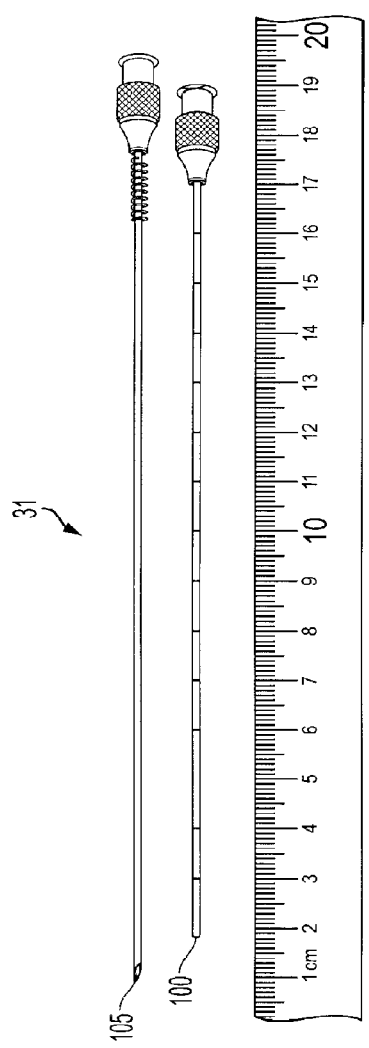
FIG. 6 is a photographic depiction of a concentric needle system for use in sub-xyphoid entry into the thorax.

The EpiNeedle, shown in FIG. 6, is a prototype of a novel telescoping-tube, concentric needle system 31 for use in sub-xyphoid entry into the thorax. The prototype consists of two concentric tubes, an inner tube, such as the puncture needle 105, and an outer tube, such as the access needle 100.

Figure 7:
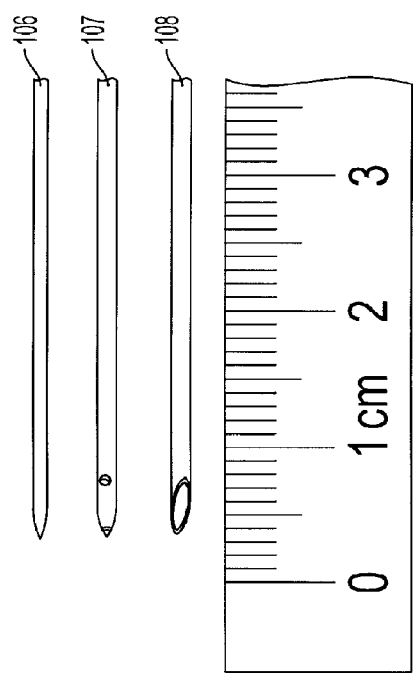
FIG. 7 is a photographic depiction of a variety of distal tip configurations of the inner needle of a concentric needle system.

By using a two-tube system, one can make the sharp-tipped inner tube retractable within the outer tube and thus extend it to pierce muscle or membrane only when needed and intended. At all other times, the sharp tip is inside of the blunt-ended outer tube, thus significantly reducing the chances of inadvertent tissue damage. The overall length of the tubing assembly can be made to specification, such as 17 cm as shown in FIG. 6. In principle, either the inner tube or the outer tube could be used as the fluid conduit for pressure sensing during intra-thoracic navigation. In an approach, the outer tube is used for that purpose, while the inner tube is introduced into the outer tube and used only for puncture (as needed) and for the introduction of contrast agent for imaging. The prototype was constructed as follows. The outer tube was made from 14 gauge 304 stainless steel hypodermic tubing (Small Parts, Inc., HTX-14R-12, regular wall), 2.11 mm (0.083 inch) outer diameter and 1.60 mm (0.063 inch) inner diameter. The length was 17 cm. The inner tube was made from 17 gauge 304 stainless steel hypodermic tubing (Small Parts, Inc., HTX-17T-12, thick wall), 1.47 mm (0.58 inch) outer diameter and 1.19 mm (0.047 inch) inner diameter. Female Luer fittings (Small Parts, Inc., LCXX-FBL0-10) were bored to the respective outer diameters in each case, and soldered onto the proximal ends of the outer and inner tubes. The outer tube was scribed with circumferential markings at 1 cm intervals and was 17 cm long, including the Luer fitting. The inner tube was 17 cm long from the distal tip to the attachment point on the Luer fitting, and was beveled to a sharp point at the distal tip. A 1-cm long spring was positioned at the proximal end of the inner tube, abutting the attachment point of the Luer fitting. When the inner tube was slid inside of the outer tube, the uncompressed spring kept the sharp point retracted inside of the distal end of the outer tube. When the inner tube's Luer fitting was pushed so as to fully compress the spring, the sharp tip of the inner tube then extended 3 mm past the distal tip of the outer tube. Three different versions of this prototype were made, as shown in FIG. 7, differing only in the details of the distal tip of the inner tube. One distal tip had the beveled tip 108 as described above, a second had a closed tip 106 with a 0.5 mm side port hole drilled approximately 4 mm from the distal end, and a third was a solid rod 107 (rather than a hollow tube) with a sharp distal tip.

Figure 8:
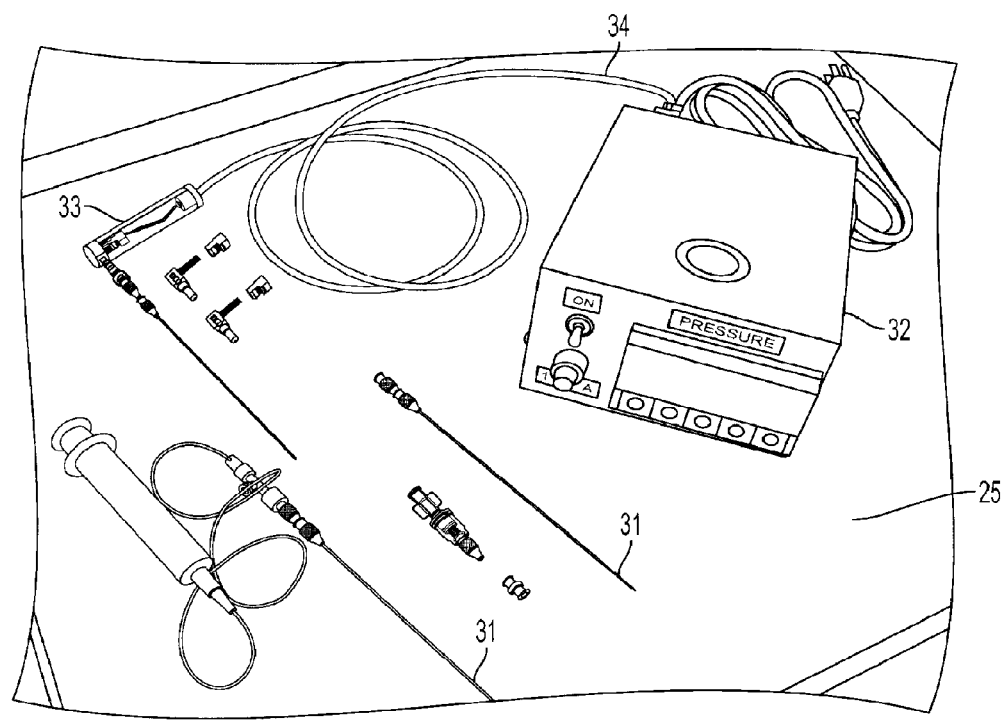
FIG. 8 is a photographic depiction of a manometric monitoring system.

A prototype of a pressure sensor 25, such as a manometric monitoring system, is shown in FIG. 8. The pressure sensor is composed of a readout box 32 with digital display, a sensor head 33, an interconnection cable 34, and additional transducer elements. In one embodiment, the pressure sensing system is capable of covering the range from −30 to +50 mm Hg.

Figure 9:
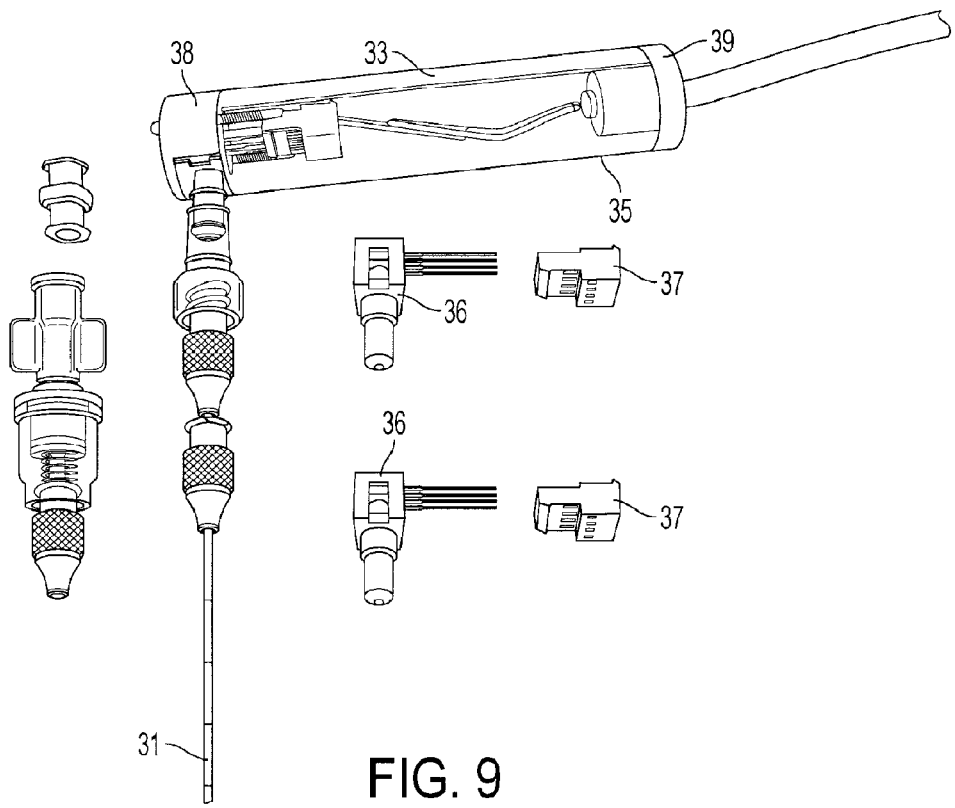
FIG. 9 is a photographic depiction of a close up view of the sensor head and other related components from a manometric monitoring system.

The inlet fitting on the sensor head was mated to the Luer connector on the EpiNeedle. In one embodiment, the inlet fitting can be gas-sterilized. A close-up view of the sensor head 33 and related components is shown in FIG. 9. The body of the sensor head is a Plexiglas™ tube 35, approximately 7.5 cm long (3 inches), 19 mm OD (0.75 inch), and 12.7 mm ID (0.5 inch). The sensor element 36 and connector 37 are positioned at the distal end of the tube 35, with the interconnection cable 34 entering the proximal end. The sensor element 36 and the interconnection cable 34 are held in place by Delrin™ end caps that were fitted into the tube. The distal end cap 38 is held in place by three small screws, while the proximal end cap 39 is friction-fit. The interconnection cable length is approximately 1 m. The outer diameter of the inlet tube on the sensor element is 5.1 mm (0.20 inch). This was about 0.25 mm (0.01 inch) larger than the inner diameter of the female inlet on the Luer adapter used to connect the sensor element to the needle. Therefore, the Luer adapter was bored 0.25 mm by lathe in order to allow a leak-tight, interference fit with the sensor element's inlet tube. The dimensions of the chassis box in which the digital display meter is mounted are 8.9× 15×20 cm (3.5×6×8 inches). The precise specifications for the cut-out needed to mount the meter on the front panel of the chassis box are given by the manufacturer. The front panel cut-outs for the fuse holder and power switch and the rear-panel cut-outs for the power and signal connections were sized to individual components that were available from general laboratory stock at the time of construction. Once the readout box was fully assembled, the polyurethane bumper feet were mounted on the bottom of the box to prevent slippage during use. The parts list for the build-out of this system is shown in Table 1.

TABLE 1

Component list for pressure sensing system.

| Item | Manufacturer | Part/Model Number |
|---|---|---|
| Chassis Box | Bud Industries Inc. | CU-2109-B |
| Digital Display Meter | OMEGA Engineering | DP25B-S |
| Pressures Transducer | OMEGA Engineering | PX26-030GV |
| Transducer Connector/Mount | OMEGA Engineering | CX136-4 |
| Signal Cable (Shielded) | OMEGA Engineering | TX-4 |
| Signal Connector (Male) | Molex | 38330-0104 |
| Signal Connector (Female) | Molex | 38331-8004 |
| Fuse (0.125 A/250 V/SB) | Littelfuse, Inc. | 313.125P |
| Fuse Holder | Littelfuse, Inc. | 03453RF1H |
| Chassis Box Bumper Feet | 3M | SJ-5003SP |
| Male Luer Lock/Female Taper | Qosina | 71677 |

The pins on the transducer fit securely into one side of the connector, and the wires from the cable are coupled into the other side of the connector and insulated with heat-shrink tubing to prevent accidental electrical shorts. The critical electrical connections for this system were those between the sensor element and the input points on the digital display meter. Table 2 shows the pin-outs and color codes that were used.

TABLE 2

Key electrical connections in the pressure sensing system.

| PX26-030GV Pin No. | Function | TX-4 Cable Wire Color | Molex Connector Set Pin No. | Chassis Box Wire Color | DP25B-S TB2 Connector Slot No. |
|---|---|---|---|---|---|
| 1 | +E (Power) | Black | 1 | Orange | 2 |
| 2 | +S (Signal) | Green | 2 | Red | 6 |
| 3 | −E (Power) | White | 3 | Green | 1 |
| 4 | −S (Signal) | Red | 4 | Yellow | 7 |

To prevent the chassis box from floating above the electrical ground point, a star ground was established on the box and earthed via the power line's ground. The manufacturer recommended the use of a ⅛ A Slo-Blo™ power line fuse. The time-delay feature of this fuse was found to be important, as fast-acting fuses could not withstand the switching transients that were generated when the display unit was turned on. Wherever possible, all signal and power junctions inside the chassis box were insulated by heat-shrink tubing in order to minimize shock hazards.

For preliminary clinical testing, the resolution of the DP25B-S digital display was set to 1 mm Hg. The intrinsic step response time of the instrument was 1 second, thus meaning that only relatively slow changes in pressure (rates ~1 Hz) could be monitored, but that was deemed satisfactory for measuring the essentially hydrostatic pressures that were expected within the thorax. The meter could be zeroed during use by pressing the "Tare" button on the front panel. None of the meter's filtering, limit-select, or gross/net measurement features were employed. For simplicity during commissioning of the apparatus, data were recorded manually and then plotted off-line. Calibrations over the pressure range of interest were carried out using an OMEGA Engineering model DPI 603 calibrator unit traceable to NIST standards. The resulting uncertainties were typically on the order of 0.5%, indicating a high quality of measurement.

Figure 10:
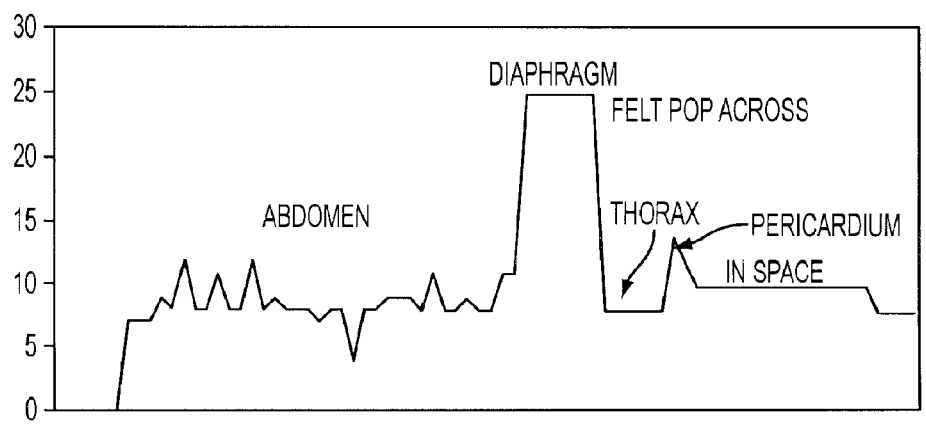
FIG. 10 is a schematic illustration of the pressures encountered as the access needle transversed the abdomen and diaphragm of a patient, and entered into the pericardial space.
Figure 11:
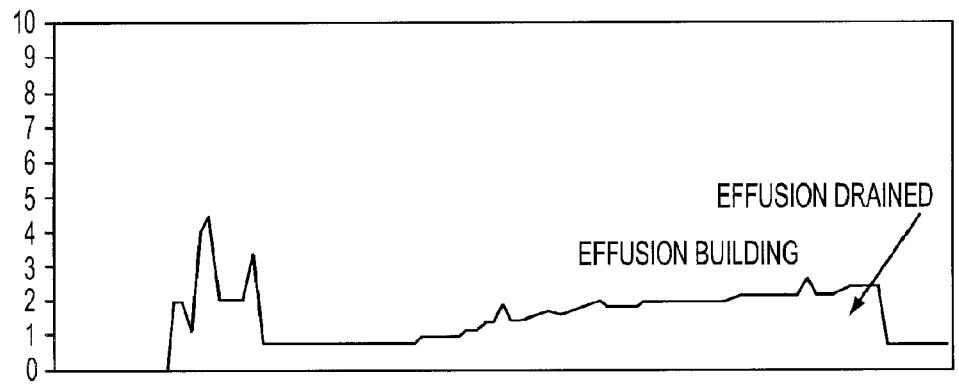
FIG. 11 is a schematic illustration of the pressures encountered during the build-up (effusion) and drainage of pericardial fluid in a patient.
Figure 12:
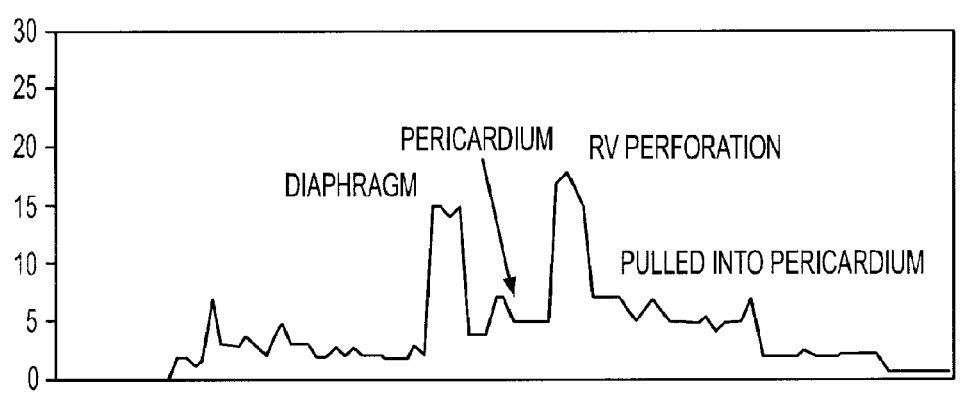
FIG. 12 is a schematic illustration of the pressures encountered as the access needle performed diaphragm transversal and right ventricular perforation.

The results are shown in FIGS. 10 through 12, which are plots of the pressures encountered as the access needle was navigated within the abdomen and thorax of each patient. The vertical scale is mm Hg in each figure. FIG. 10 graphically illustrates the traversal of the abdomen and diaphragm, and entry into the pericardial space. FIG. 11 graphically illustrates the observation of build-up (effusion) and drainage of pericardial fluid in a patient that had previously undergone a coronary artery bypass graft. FIG. 12 graphically illustrates the pressure-based observation of diaphragm traversal and right ventricular perforation. Since the data were to be taken manually, precision timing was not sought. However, the procedures required approximately 15 minutes each.

Example/Experimental Result No. 2

Figure 13:
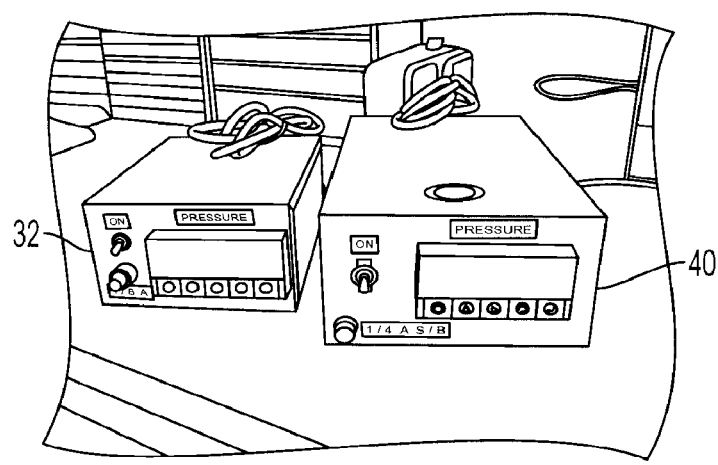
FIG. 13 is a photographic depiction of the front view of two prototypes of a pressure read-out box.
Figure 14:
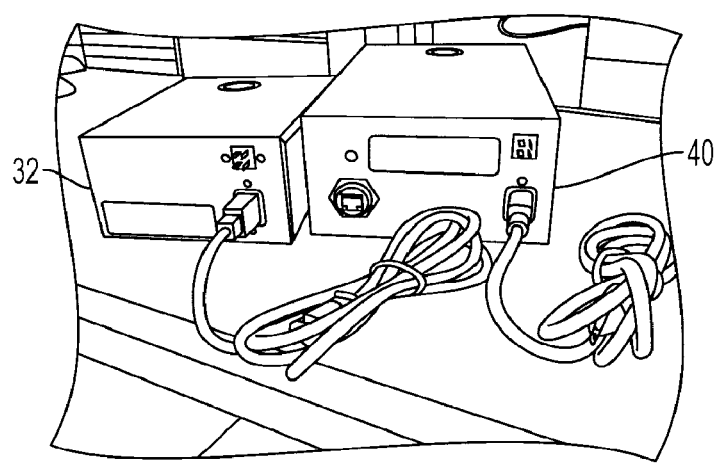
FIG. 14 is a photographic depiction of the rear view of two prototypes of a pressure read-out box.

A prototype of an access needle and pressure measurement system was used in human clinical trials during the course of epicardial procedures. The manometric monitoring system was designed for optimal operation over the pressure range from roughly −30 to +50 mm Hg. Its inlet fittings mated with gas-sterilized Luer connectors, for ease of clinical assembly and use. The sensor head and related components shown in FIG. 9 were used in this prototype. To enable data acquisition capabilities and thus automate the measurement of the intrathoracic pressures, a more sophisticated digital display meter was implemented in the prototype. We chose an OMEGA Engineering DP41-B for this purpose, since it is capable of either Ethernet or serial communications. The dimensions of the chassis box that housed it are 10.2×17.3×30.3 cm (4×7× 12 inches). The precise specifications for the cut-out needed to mount the meter on the front panel of the chassis box are given by the manufacturer. The front panel cut-outs for the fuse holder and power switch and the rear-panel cut-outs for the power, signal, and I/O connections were sized to individual components that were available from general laboratory stock at the time of construction. Once the readout box was fully assembled, the polyurethane bumper feet were mounted on the bottom of the box to prevent slippage during use, and front and rear labels were placed as needed. Table 3 provides a listing of the components needed to construct the pressure read-out box. FIG. 13 shows the front view of the readout box implemented in the first prototype 32 and the readout box from the second prototype 40. FIG. 14 shows the rear view of the readout boxes.

TABLE 3

Component list for pressure sensing system.

| Item | Manufacturer | Part/Model Number |
|---|---|---|
| Chassis Box | Bud Industries Inc. | CU-2111-B |
| Digital Display Meter | OMEGA Engineering | DP41-B |
| Pressures Transducer | OMEGA Engineering | PX26-030GV |
| Transducer Connector/Mount | OMEGA Engineering | CX136-4 |
| Signal Cable (Shielded) | OMEGA Engineering | TX-4 |
| Signal Connector (Male) | Molex | 38330-0104 |
| Signal Connector (Female) | Molex | 38331-8004 |
| Fuse (0.250 A/250 V/SB) | Littelfuse, Inc. | 313.250P |
| Fuse Holder | Littelfuse, Inc. | 03453RF1H |
| Chassis Box Bumper Feet | 3M | SJ-5003SP |
| Male Luer Lock/Female Taper | Qosina | 71677 |

The critical electrical connections for this system were those between the sensor element and the input points on the digital display meter. Table 4 shows the pin-outs and color codes that were used. Each wire within the chassis box was labeled by pin number so there could be no confusion during connection or re-connection. To prevent the chassis box and digital display meter from floating above the electrical ground point, a star ground was established on the box and earthed via the power line's ground, as well as to P3-3 and P1-3. The manufacturer recommended the use of a ¼ A Slo-Blo™ power line fuse. The time-delay feature of this fuse was found to be important, as fast-acting fuses could not withstand the switching transients that were generated when the display unit was turned on. Wherever possible, all signal and power junctions inside the chassis box were insulated by heat-shrink tubing in order to minimize shock hazards.

TABLE 4

Key electrical connections in the pressure sensing system.

| PX26-030GV Pin No. | Function | TX-4 Cable Wire Color | Molex Connector Set Pin No. | Chassis Box Wire Color | DP41-B Connector/ Slot No. |
|---|---|---|---|---|---|
| 1 | +E (Power) | Black | 1 | White | P9-1 |
| 2 | +S (Signal) | Green | 2 | White | P9-2 |
| 3 | −E (Power) | White | 3 | White | P3-1 |
| 4 | −S (Signal) | Red | 4 | White | P9-3 |

Figure 15:
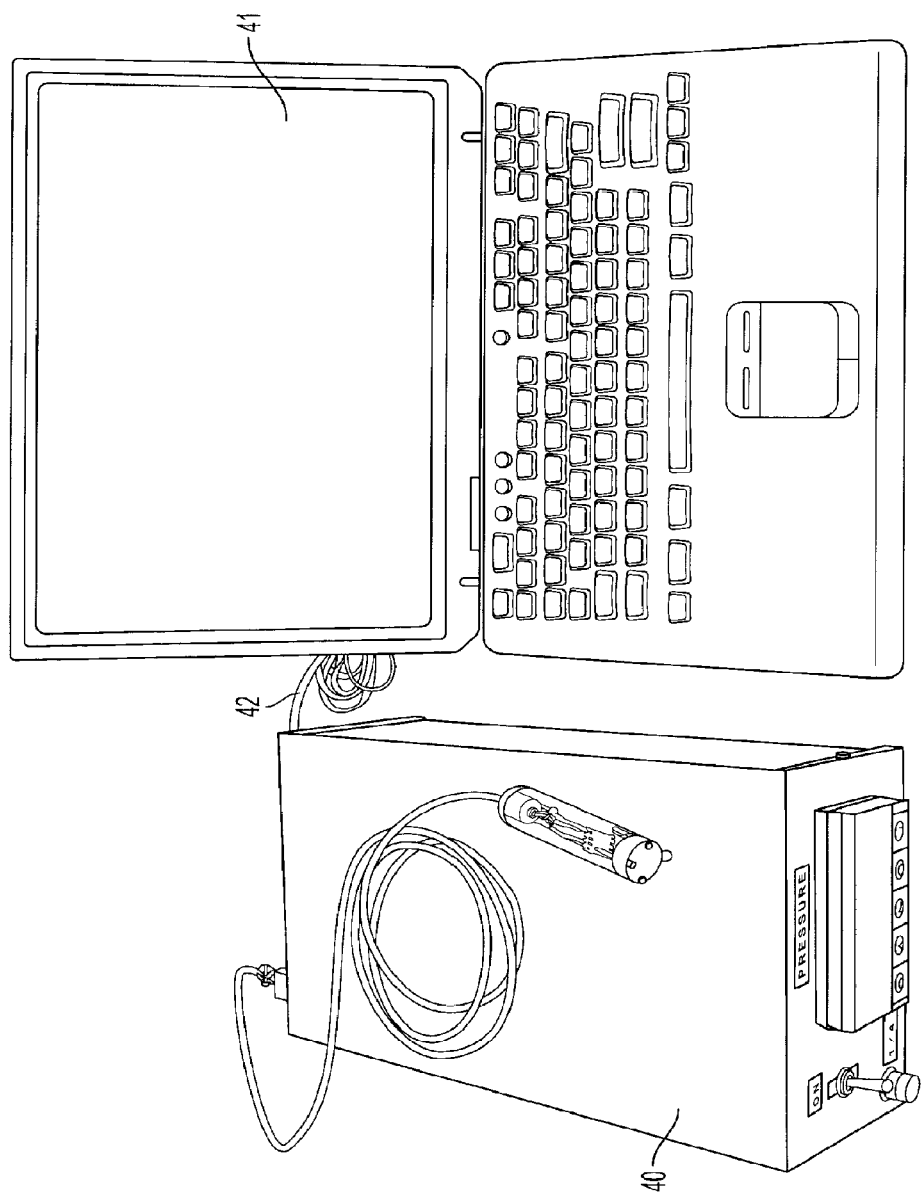
FIG. 15 is a photographic depiction of the pressure readout box and the laptop computer used for data acquisition.

The Ethernet and serial communications options for I/O from the DP-41-B panel meter were tested, and it was found that a direct serial option sidestepped some latencies in the Ethernet data conversion process, with the result that read-out rates of 17 to 20 Hz were possible. This was sufficiently fast to obtain a profile of individual heartbeats at normal physiological rates (60 beats per minute, i.e., 1 Hz), so the data acquisition was handled via the serial communications option. An IBM Thinkpad T30 laptop computer running the Windows XP Professional operating system was used to store and process the data. FIG. 15 shows a photo of the pressure read-out box 40 and the laptop computer 41, interconnected by a serial cable 42. The laptop runs a custom-written Lab-VIEW™ program for data storage, processing and presentation.

It should be appreciated that any computer or computer processor, as well as any graphical interface or printer and storage, may implemented with any of the present invention embodiments discussed herein.

A National Instruments LabVIEW™ virtual instrument (VI) was developed with the goal of acquiring, analyzing, and presenting data from the DP41-B digital panel meter in real time at a rate fast enough to observe pressure waves in the pericardial space at twice the frequency of a heartbeat.

The front panel of the VI that was programmed to appear on the laptop's display contains various indicators and switches which would be needed by the clinician during an epicardial procedure. An important element of the front panel is the waveform chart, which can display one of two things. Using the F5 button as a toggle switch, the waveform chart will either display the actual pressure readings from the DP41-B sensor, or the time-derivative of the readings. Also displayed on the pressure waveform are the high and low alarms values, which the clinician can set. The program then monitors the pressures and alerts the clinician if it appears the limiting values are in danger of being breached during surgery. Alarm limits can also be set for the derivative waveform, to enable indication of a differential breach alarm that could indicate a drastic pressure drop, eg., associated with puncture of the diaphragm or some other such situation which the clinician would need to know has occurred. Underneath the waveform chart is an indicator that displays either the pressure reading itself (if it is within the range of the high and low alarms) or the text message "ALARM!!!" (if the limiting pressure values are breached). To the right of the alarm string indicator, is an input path indicator for a *.wav file which can be used to annunciate that a large pressure drop has occurred due to penetration of the diaphragm. This *.wav audio file will play only when the pressure differential is exceeded, thus alerting the clinician without the need for any other interaction with the program.

Figure 16:
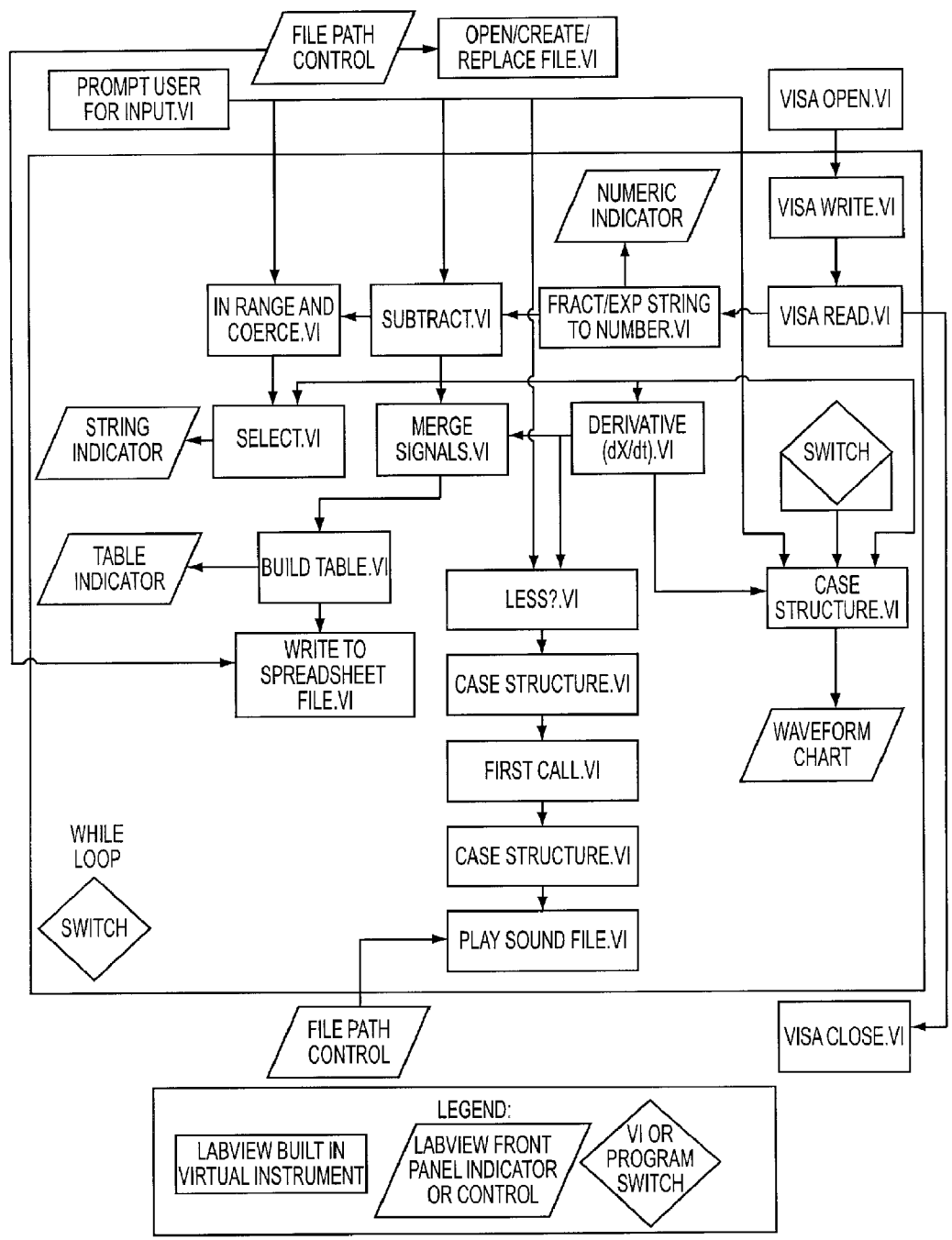
FIG. 16 is a schematic block diagram of the interactions within a software program.

FIG. 16 shows a block diagram of the LabVIEW™ VI's in the system control program, and illustrates how the various VI's interact within the LabVIEW™ program. The first step in the algorithm is a prompt for user input which the program requests in order to initialize the values for the variables "Tare", "Max", "Min", and "Breach Differential." The first value, "Tare", allows for the automatic zeroing of the pressure sensor. For instance, if the current open-air reading of the pressure sensor is a non-zero value, that value can be inserted into "Tare" for an in-program zeroing of the pressure. "Max" is the input for the high alarm in mm Hg, which the clinician does not wish to breach in fear of puncturing the right ventricle. "Min" is the input for the low alarm in mm Hg that might signal the close proximity of the negative pressure in the pleural space. "Breach Differential" is the pressure drop that indicates that the diaphragm is being punctured.

The main area of the program is a while loop, which continuously runs until the "End" key is toggled by the clinician. However, there are a few VI's which run only once; prior to the activation of the while loop. The "Open/Create/Replace File" VI replaces the existing saved pressure and derivative data from previous runs with the new data from the current run. Also, the start of the data collection from the serial communications port begins with the "VISA Open" VI, which opens the port based on saved configuration settings from the Measurement and Automation configuration software. (VISA stands for "Virtual Instrument Software Architecture, and it is the library of functions that one uses to communicate with the VI driver software.) The serial termination character of the VISA Resource Name line is also set to the control value of 13. This VISA Resource Name line serves as the reference for all the other VISA VI's.

The start of the while loop begins by querying and parsing the pressure sensor readings from the DP41-B device via the VISA serial communications line that has been established. The command "*X04" is written to the serial port using the "VISA Write" VI, which requests the data measurement value from the device in decimal format. The "VISA Read" VI then reads 4096 bytes from the serial communications port and returns a string which contains the string "X04" followed by the decimal value for the pressure readings. The "Fract/Exp String to Number" VI then converts the returned string to a LabVIEW™ double while cutting off the "X04" at the beginning of the string. The newly created double is the value in the program, which represents the measurement being read currently by the sensor. The value is then zeroed in the program by subtracting out the value entered into "Tare" during the original user-input session.

The zeroed value is then passed into multiple functions. It is first passed into the "In Range and Coerce" VI, to see if it falls in the range of the two alarms. The high and low bounds passed into the range VI are the values entered into the "Max" and "Min" inputs from the original user-input session. If the current value is between the two alarms, the VI returns a Boolean value of true. If not, the "In Range and Coerce" VI returns a Boolean value of false. The Boolean value returned by the VI is passed into the "Select" VI, which passes a different string into the "Alarm" indicator on the front panel based on the Boolean value it receives. If the VI receives a value of true, then it simply passes the current reading into the string indicator. If the VI receives a value of false, indicating the measured pressure is outside of the alarm range, it passes a bright red text string, which says "ALARM!!!" to the front panel indicator. The zeroed pressure value is also passed into the "Derivative (dX/dt)" VI, which takes an ongoing differential of the signal as the while loop cycles continuously. This derivative signal and the original zeroed pressure signal are passed into a case structure and then to the front panel waveform chart. The case structure serves as the switch between displaying the pressure reading, or its derivative on the front panel. When toggled to true using the F5 key, the case structure takes the zeroed pressure reading, and merges the signal with the alarm values, to be displayed on the waveform chart. When toggled to false, the case structure takes the derivative value, and merges the signal with the "Breach Differential" value, to be displayed on the front panel waveform chart. The final use of the zeroed pressure reading is to be logged for later data retrieval. Using the "Merge Signals" VI that was also used in the previous case structure, the zeroed reading is merged with the derivative reading into one dynamic signal to be passed into the "Build Table" VI, to be constructed into a table. This table saves all the data from the current run, is shown in the bottom of the front panel, and is also saved as an Excel spreadsheet in a file location designated by the clinician.

The final section of the while loop involves the derivative signal. The derivative is continuously compared to the original "Breach Differential" input value using a comparison VI, and if the current derivative it is greater than that value, a Boolean value of false is passed into a new case structure, otherwise true is returned. The Boolean value returned by the comparison VI is the switch for the case structure. Once the derivative drops below the "Breach Differential" value, indicating a penetration of the diaphragm, a Boolean value of true activates a case structure, which plays the *.wav audio file selected on the front panel by the clinician. This serves as the program's way of allowing an alarm to trigger, which will not startle the physician, and does not require any interaction with the program to disable.

Figure 17:
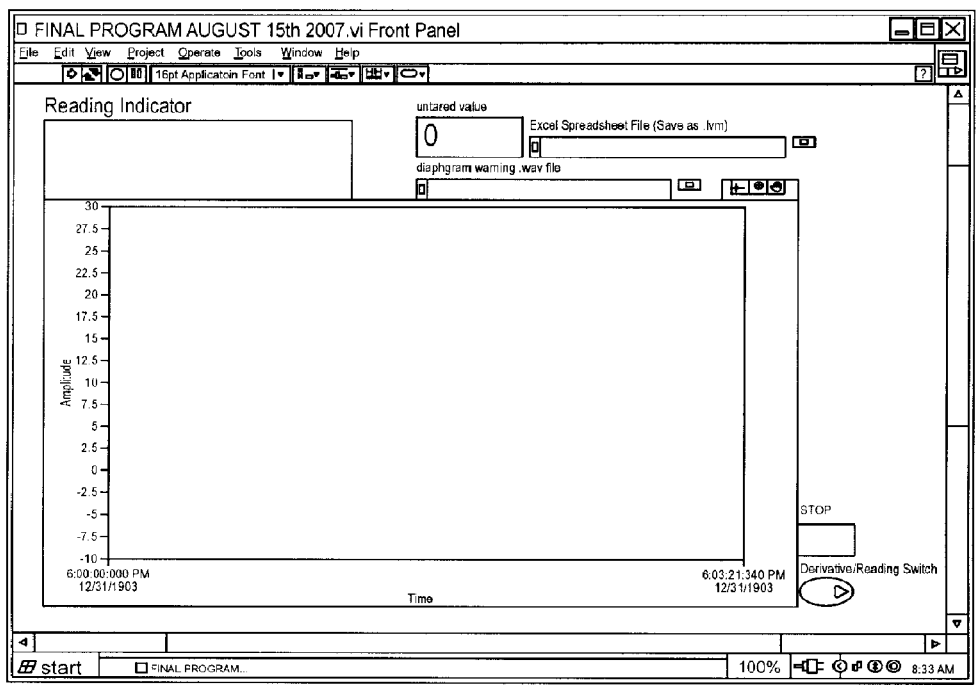
FIG. 17 is a schematic display of the data acquisition computer's screen when the software program is loaded and ready for use.
Figure 18A:
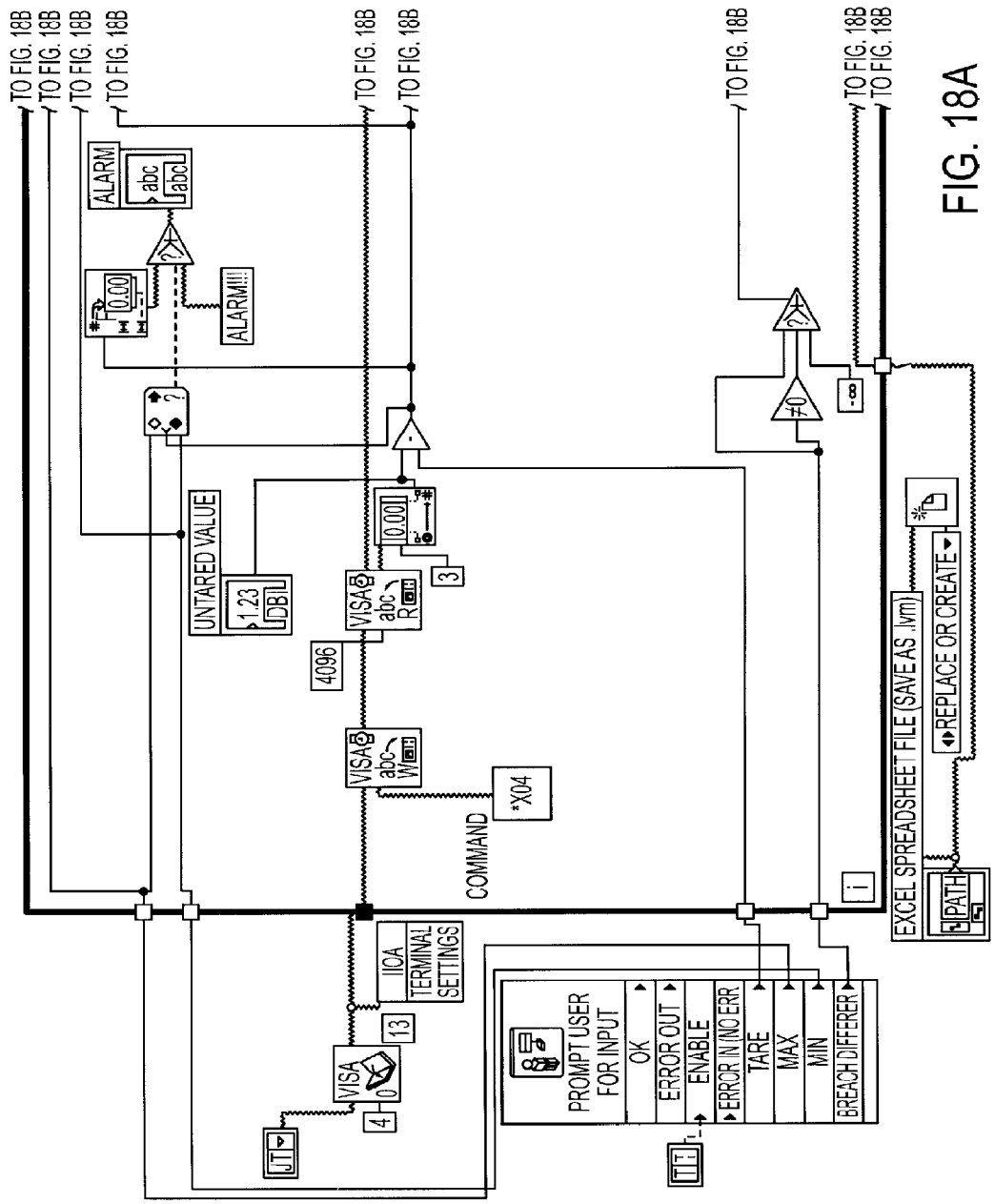

The while loop runs continuously, writing and reading to and from the serial communications port to retrieve the pressure data from the device. The VI's inside the while loop continuously alter and present the signal in the front panel and save the analyzed data at each step of the way using the methods described above. When the "End" key is toggled on the keyboard, it switches off the while loop and discontinues the program. The final step involves closing the serial port utilizing the "VISA Close" VI so that other software programs may access the port after the VI's completion. FIG. 17 shows a screen shot of the front panel as seen on the laptop's display when the LabVIEW™ program is loaded and ready for use. FIGS. 18A-B shows a screen shot of the LabVIEW™ VI assembly in its native block diagram form in a left side and right side interconnecting portions, respectively, for illustration purposes.

Figure 19:
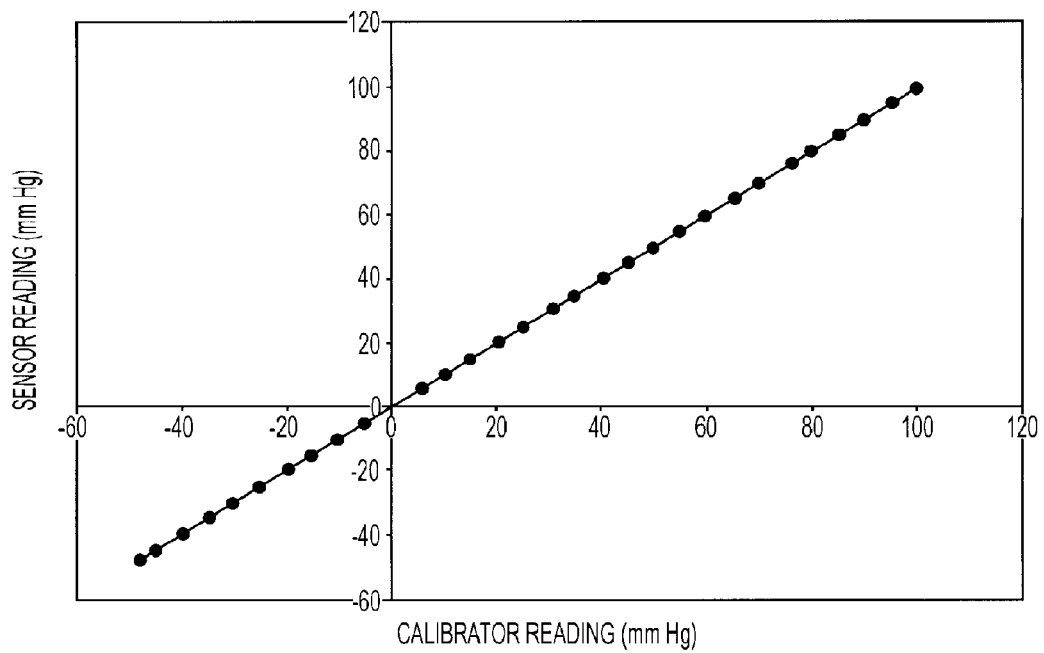
FIG. 19 is a graphical illustration of the calibration curve obtained during calibration testing of the overall pressure sensing and data acquisition system.

An OMEGA Engineering model DPI 603 portable pressure calibrator was used to apply known positive and negative pressures to the PX26-030GV transducer in the sensor head assembly in order to calibrate the overall pressure sensing and data acquisition system. The operating procedure used for carrying out such calibration tests is straightforward, and is given in detail elsewhere. FIG. 19 shows a typical data plot obtained during the course of the calibration studies for the OMEGA Engineering model PX26-030GV transducer used in these experiments. We found no deviations from linearity in excess of the 1% level claimed by the manufacturer.

Testing of this second prototype of the manometric-monitoring access system was carried out to demonstrate that the access system could clearly resolve the difference in the frequency and amplitude of the pressure waves measured in the thoracic space versus those in the pericardial space (whatever their sources might be). This would enable the clinician to know when they have passed from the one region into the other. A significant advantage could accrue from such a finding: the pressure measurements would make it instantly obvious when the needle has perforated the right ventricle, thus indicating that pullback is essential immediately.

Case 1 involved an epicardial ablation procedure to treat a ventricular tachycardia, which could not be corrected endocardially. This case did not involve attaching the pressure system to the introducer needle itself. Instead, the pressure system was attached to the introducer sheath after surgical insertion, and pressure readings were taken inside the pericardium at the sheath's tip and as the sheath was removed from the body. The transducer coupled to the surgical line through a 4-way stopcock. The surgical tubing, pressure transducer, and stopcock were all filled with saline utilizing an attached 25 ml syringe. First, only the syringe and transducer ports were open with the transducer disconnected from the system, and those two ports were filled with saline from the syringe. After the tubing port was opened the entire system was filled with saline and flushed several times in order to evacuate as much entrained air as possible from the lines. During data collection, the sheath was attached to the fully flushed surgical tubing to make the entire system, from sheath tip to transducer, one movable liquid column of saline. The location of the sheath inside the pericardium was earlier verified by the distribution of contrast agent around the cardiac silhouette. The system was then left in place in the pericardium so that data could be acquired and saved to an Excel spreadsheet.

Figure 20:
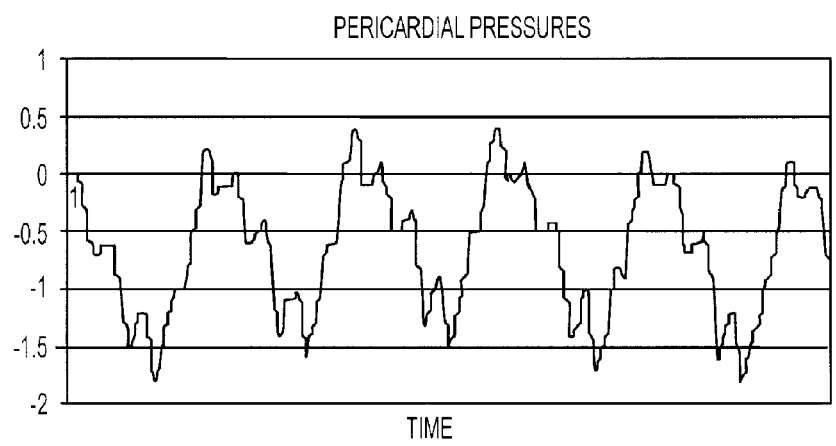
FIG. 20 is a graphical illustration of pressure readings from inside the pericardium.

The pressure readings from inside the pericardium are plotted in FIG. 20. The measured waveform consists of two components: a slow one presumably associated with the breathing rate and a fast one presumably driven by the heart rate. The total span of the full data train is 28 seconds. There are roughly 5.25 of the longer cycles and 26 of the shorter ones, hence the rates of these components are 11.25 breaths per minute and 55.7 beats per minute, respectively. In fact, these empirically deduced values are almost identical to intubation-controlled breathing rate and the actual recorded heart rate of the patient, as shown in Table 5. These results demonstrate that the pericardial pressure is influenced by both the lungs and the heart.

TABLE 5

Comparison of pressure-derived and actual breathing and heart rates for Case 1.

| | Heart Rate | Respiration Rate | Comments |
|---|---|---|---|
| Inferred from data | 55.7 beats/minute | 11.25 breaths/minute | Confirmed by FFT |
| Actual values | 55 beats/minute | 11 breaths/minute | Controlled clinically |

Figure 21:
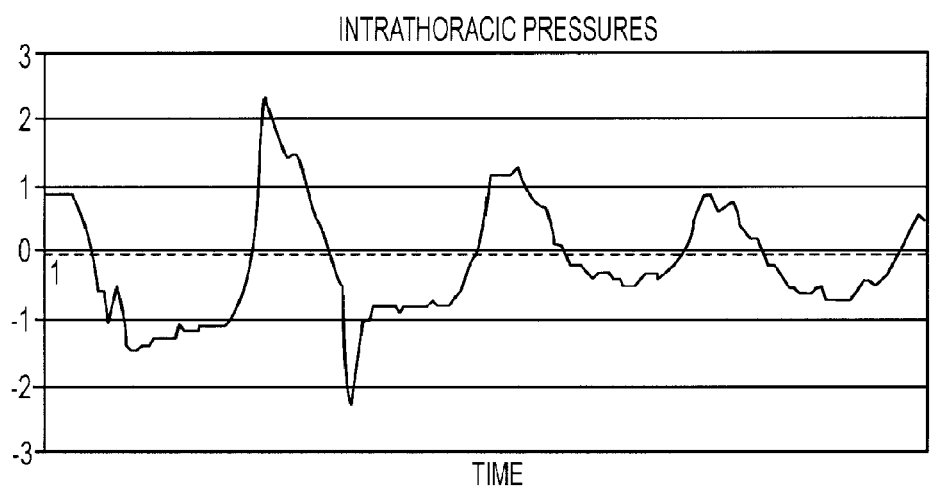
FIG. 21 is a graphical illustration of measurements of intrathoracic pressure.

As the sheath was withdrawn from the pericardium and into the thorax, the pressure waveform lost the fast component, thus indicating that the forced respiration was now the principal driving source within the thoracic space. A 22 second sample of the data taken when the sheath was in the thoracic space is shown in FIG. 21. This data train is not as regular in its structure as that of FIG. 20, and we attribute this to possible fluid instability inside of the sheath, which had a larger inner diameter than that of the introducer needle and was hence more prone to leakage. A second consideration was degradation of the data acquisition rate from 17 Hz to 7 Hz as the laptop's memory and buffers filled. Fortunately, 7 Hz was still about three times faster than Nyquist frequency for the observation of the heart beat, thus allowing us to conclude that the heart-driven pressure component was absent from the thoracic measurements. The breathing rate as derived from these data was approximately 10.9 breaths/minute, within 1% of the known clinically-controlled rate.

Figure 22:
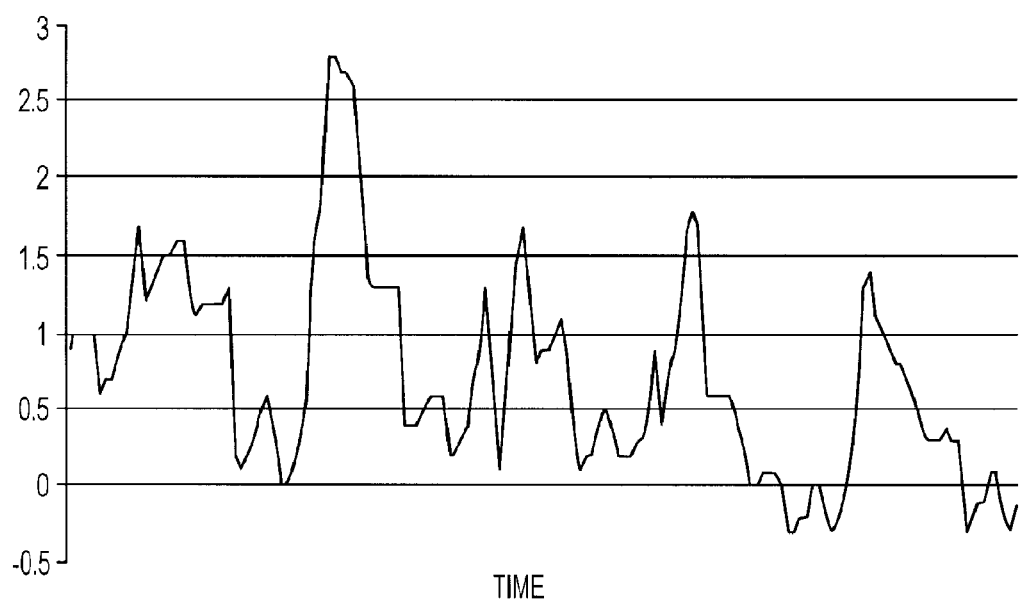
FIG. 22 is a graphical illustration of measurements of pericardial pressure.

Case 2 involved a similar set of measurements taken on a second patient, who was also being treated for ventricular tachycardia that could not be corrected endocardially. The clinical experimental arrangement was the same as for the first case. The data for approximately 8,000 pericardial pressure measurements were acquired over an 18 minute period, and a sample of the data are shown in FIG. 22. A downward drift in pressure was noted in the measurements made during the course of this second case. (This was found to be a correctable artifact of the measurement system.) An assessment of the results are shown in Table 6.

TABLE 6

Comparison of pressure-derived and actual breathing and heart rates for Case 2.

| | Heart Rate | Respiration Rate | Comments |
|---|---|---|---|
| Inferred from data | 45 beats/minute | 10.9 breaths/minute | Confirmed by FFT |
| Actual values | 44 beats/minute | 11 breaths/minute | Controlled clinically |

Figure 23A:
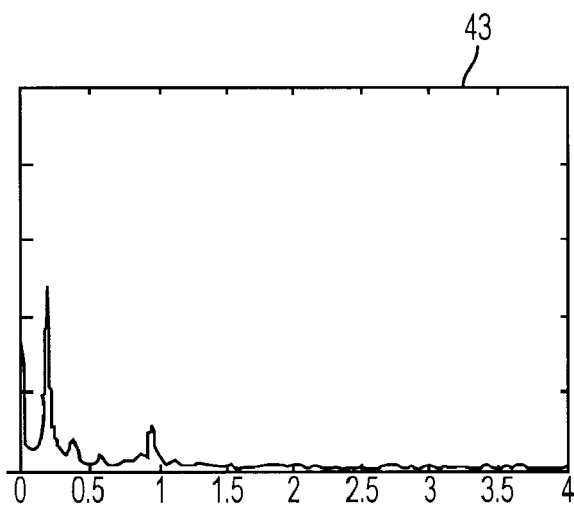
FIGS. 23(A)-(B) are graphical illustrations of spectra of the pericardial signal and the intrathoracic signal. Spectra of the pericardial signal (left, FIG. 23(A)) and the intrathoracic signal (right, FIG. 23(B)).
Figure 23B:
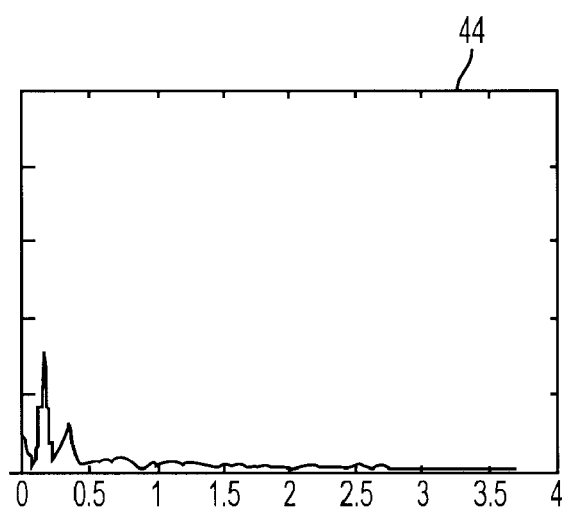

Off-line analysis of the data was carried out using MATLAB® software. The spectral content of the pericardial signal 43 and the intrathoracic signal 44 from Case 1 is shown in FIGS. 23(A)-(B), respectively. As seen there, the pressure measurements made in the pericardium reveal peaks at just under both 0.2 Hz and 1.0 Hz, corresponding to the breathing and heart-beat rates, respectively. However, for those from the intrathoracic cavity, the peak at just under 1.0 Hz is absent, indicating that the measurement system can indeed tell the clinician when they have moved from the one space into the other. The peak at approximately 0.4 Hz in the intrathoracic data is the 1$^{st}$ harmonic frequency of the fundamental mode of the breathing frequency. This harmonic is also present in the pericardial signal, but at a lower intensity level.

Because the data rates are relatively slow, it will be possible to use a fast FFT algorithm to carry out the signal analysis in near real time, thus presenting the clinician with a spectral plot that could be used as an instantaneous guide for informing them when the introducer has entered the pericardial space, when there has been a perforation, etc. The rise and fall of the relative signal strengths as presented on the spectrum would be clear evidence of such events, thus constituting a type of manometric endoscopy unique to this type of subxyphoid approach.

Another embodiment of the prototypes discussed above involves the incorporation of a Qosina model no. 80360 Luer-fitted check valve into the pressure lines to enable filling without the need to make and break external fluidic connections. Another embodiment involves the use of a different type of pressure sensor, for example the World Precision Instruments, Inc. model BLPR2, in which the detector element is situated perpendicular to the wall of the tubing containing it, rather than in-line with the tubing. This allows for flow-through priming of all the parts rather than back-fill priming, thus making it possible to completely flush out any entrained air bubbles.

Example/Experimental Result No. 3

Figure 24:
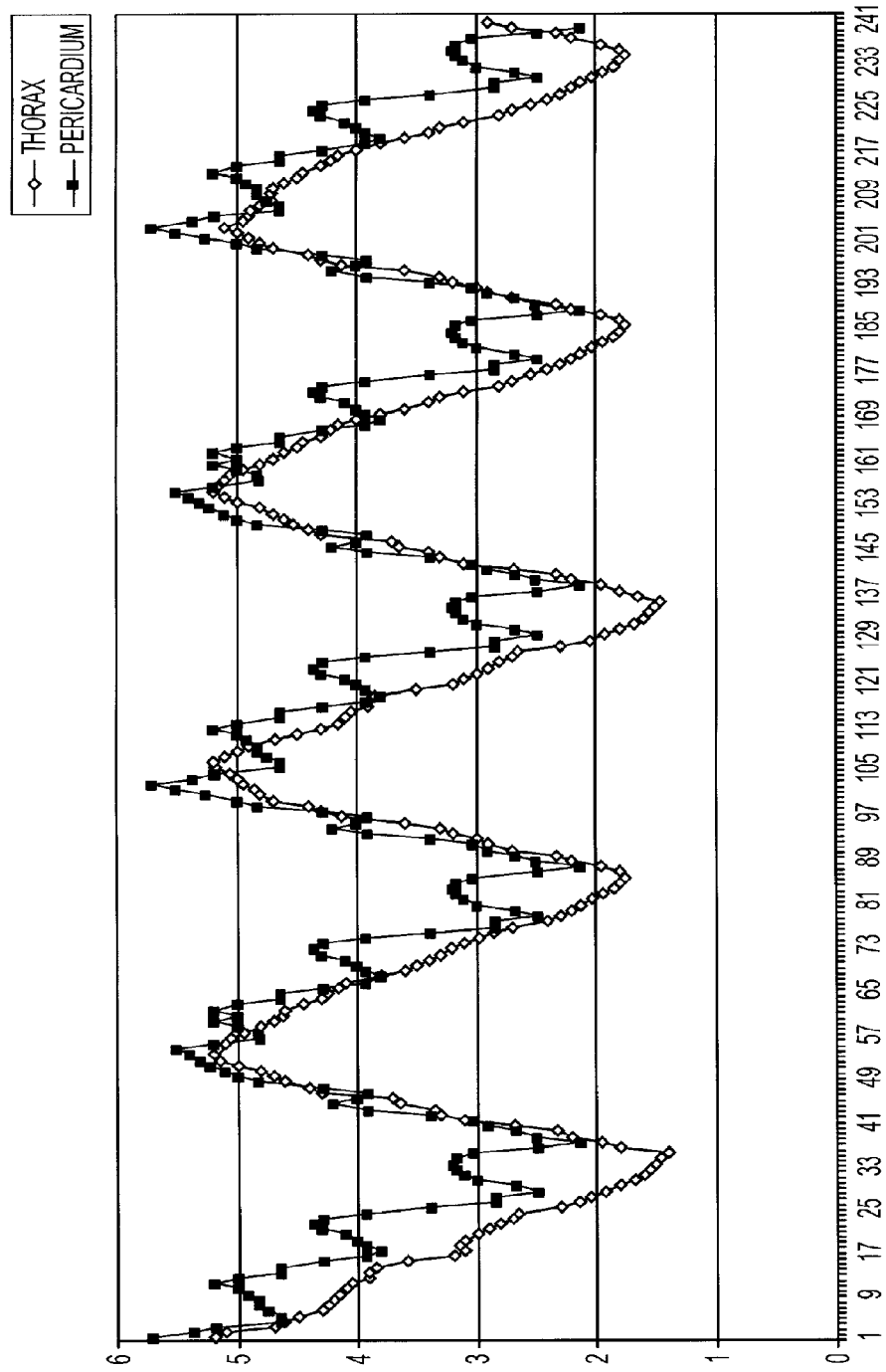
FIG. 24 is a graphical illustration of pressure readings from inside the thorax pericardium.

FIG. 24 is a schematic illustration of pressure readings from inside the thorax and pericardium. The lower row of points in the figure shows that in a total of 17 patients, the sensor system resolved that there was a low-frequency component to the pericardial pressure wave that was associated with the (intubated) breathing rate of 0.2 Hz (five breaths per minute). Meanwhile, the upper series of data points in the figure show that the sensor system resolved that there was a higher-frequency component to the pericardial pressure wave that was associated with the rate of heartbeat of the patients, typically 1.0 to 1.2 Hz (roughly 60 beats per minute).

REFERENCES CITED

The following patents, applications and publications as listed below and throughout this document are hereby incorporated by reference in their entirety herein.

The devices, systems, compositions and methods of various embodiments of the invention disclosed herein may utilize aspects disclosed in the following references, applications, publications and patents and which are hereby incorporated by reference herein in their entirety:

U.S. Patent Documents

| 7,101,362 | September 2006 | Vanney | 604/523 |
| 7,037,296 | May 2006 | Kadziauskas et al. | 604/294 |
| 6,554,809 | April 2003 | Aves | 604/272 |
| 6,551,289 | April 2003 | Higuchi et al. | 604/272 |
| 6,273,877 | August 2001 | West et al. | 604/264 |
| 6,231,518 | May 2001 | Grabek et al. | 600/508 |
| 6,206,004 | March 2001 | Schmidt et al. | 128/898 |
| 6,156,009 | December 2000 | Grabek | 604/117 |
| 5,972,013 | October 1999 | Schmidt | 606/185 |
| 5,843,048 | December 1998 | Gross | 604/264 |
| 5,725,504 | March 1998 | Collins | 604/165 |
| 5,669,882 | September 1997 | Pyles | 604/164 |
| 5,484,423 | January 1996 | Waskönig et al. | 604/272 |
| 4,349,023 | September 1982 | Gross | 128/214.4 |

Foreign Patent Documents

| EP | 1 129 681 A1 | September 2001 |
| WO | 95/10319 | April 1995 |

Other Publications

M. A. Frölich et al., "Pioneers in Epidural Needle Design," Anestheis and Analgesia, vol. 93, pp. 215-220, (2001).

Arrow International Corporation, AN-05505 Epidural Needle, www.arrowintl.com/products/boms/AN05505.asp?cat=17&item=AN-05505&xsec=(accessed Feb. 13, 2007).

E. Sosa et al., "Epicardial Mapping and Ablation Techniques to Control Ventricular Tachycardia," Journal of Cardiovascular Electrophysiology, Vol. 16, pp. 449-452, (2005).

E. Sosa et al., "Nonsurgical Transthoracic Epicardial Approach in Patients with Ventricular Tachycardia and Previous Cardiac Surgery," Journal of Interventional Cardiac Electrophysiology, Vol. 10, pp. 281-288, (2004).

d'Avila, A., Scanavacca, M., and Sosa, E., "Transthoracic epicardial catheter ablation of ventricular tachycardia," Heart Rhythm, Vol. 3, pp. 1110-1111, (September, 2006).

Sosa, E. and Scanavacca, M., "Percutaneous Pericardial Access for Mapping and Ablation of Epicardial Ventricular Tachycardias," Circulation, Vol. 115, pp. e542-e544, (May, 2007).

Thomas, P. S., Gerson, J. I., and Strong, G., "Analysis of Human Epidural Pressures," Regional Anesthesia, Vol. 17, pp. 212-215, (July-August 1992).

Frölich, M. A. and Caton, D., "Pioneers in Epidural Needle Design," Anesthesia & Analgesia, Vol. 93, pp. 215-220, (2001).

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A system for accessing one or more locations of a subject, said device comprising:
    an elongated member having a distal end and a proximal end;
    a pressure sensor in communication with said elongated member;
    a processor configured to:
        receive sensed information from said pressure sensor, and
        to detect a change in a sensed pressure frequency based on the sensed information;
    a reading system configured to present the pressure frequency to a user; and
    an alarm that is configured to provide an alert in response to a change in the sensed pressure frequency.

2. The system of claim 1, wherein said elongated member is a needle or axial device.

3. The system of claim 2, wherein said elongated member is a needle configured to access the thorax.

4. The system of claim 1, wherein said processor is further configured to be able to differentiate between approximately 0.2 Hz and 1.0 Hz.

5. The system of claim 1, wherein said reading system is further configured to interpret the pressure frequency to identify whether said elongated member has entered an inappropriate location of the subject.

6. The system of claim 1, wherein said reading system is configured to present the pressure frequency in substantially real time while said elongated member is being advanced.

7. The system of claim 1, wherein said elongated member includes at least one distal aperture located at said distal end of said elongated member, at least one proximal aperture located at said proximal end of said elongated member, and at least one proximal lumen in communication with said at least one distal aperture and said at least one proximal aperture.

8. The system of claim 7, further comprising multiple fluid flow channels in communication with said at least one proximal aperture.

9. The system of claim 7, further comprising a guide wire configured to be inserted through said at least one proximal aperture and withdrawn from said distal aperture.

10. The system of claim 7, further comprising a plurality of distal apertures.

11. The system of claim 1, further comprising a puncture needle coaxially aligned with said elongated member.

12. The system of claim 11, further comprising a restoring force device in communication with said puncture needle.

13. The system of claim 1, wherein said pressure sensor is configured to detect regions of positive pressure and those of negative pressure.

14. The system of claim 1, wherein said elongated member is configured to provide a guideway for positioning of at least one of a guide wire, a sheath, a catheter, or any combination thereof, for use in a medical procedure.

15. A method for accessing one or more locations of a patient using an elongated member associated with a pressure sensor, said method comprising:
    inserting the elongated member into the patient's body and accessing the one or more locations;
    sensing pressure information in the one or more locations with the pressure sensor associated with the elongated member;
    determining pressure frequency information in said one or more locations based on the pressure information; and
    at least one of presenting the pressure frequency information to a user such that changes in the pressure frequency can be observed by the user, and providing an alarm based on changes in the pressure frequency information.

16. The method of claim 15, wherein the elongated member is a needle or axial device.

17. The method of claim 15, wherein said one or more locations comprise the thorax and middle mediastinum.

18. The method of claim 15, further comprising determining whether the elongated member has entered an inappropriate location based on the pressure frequency information.

19. The method of claim 15, comprising presenting the pressure frequency information to the user such that changes in the pressure frequency can be observed by the user, and providing the alarm based on changes in the pressure frequency information.

20. The method of claim 15, wherein said one or more locations comprise at least a portion of an organ of the patient, said organ comprising at least one of hollow organs, solid organs, parenchymal tissue, stromal tissue, or ducts.

* * * * *